(12) United States Patent
Levin et al.

(10) Patent No.: US 9,995,833 B1
(45) Date of Patent: Jun. 12, 2018

(54) NUCLEAR MEDICINE IMAGING SYSTEMS AND METHODS HAVING A SECONDARY MECHANISM FOR CONTROLLING A DETECTOR HEAD

(71) Applicant: General Electric Company, Schenectady, NY (US)

(72) Inventors: Ilan Levin, Tirat Carmel (IL); Noam Perlis, Tirat Carmel (IL); Refael Dayan, Tirat Carmel (IL); Moty Levy, Tirat Carmel (IL); Roee Khen, Tirat Carmel (IL); Raed Khamaisi, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 0 days. days.

(21) Appl. No.: 15/452,213

(22) Filed: Mar. 7, 2017

(51) Int. Cl.
*G01T 7/08* (2006.01)
*G01T 1/164* (2006.01)
*G01T 1/29* (2006.01)
*A61B 6/00* (2006.01)

(52) U.S. Cl.
CPC .............. *G01T 7/08* (2013.01); *A61B 6/4266* (2013.01); *G01T 1/1642* (2013.01); *G01T 1/2985* (2013.01)

(58) Field of Classification Search
CPC ......... G01T 1/1642; G01T 1/166; G01T 7/08; A61B 6/4266
See application file for complete search history.

(56) References Cited

U.S. PATENT DOCUMENTS

| | | | |
|---|---|---|---|
| 4,652,758 A * | 3/1987 | Barfod | A61B 6/0457 |
| | | | 250/363.04 |
| 5,486,700 A | 1/1996 | Silberklang et al. | |
| 7,827,635 B2 | 11/2010 | Wang et al. | |
| 8,338,788 B2 * | 12/2012 | Zilberstein | G01T 1/1611 |
| | | | 250/363.04 |
| 9,295,439 B2 | 3/2016 | Hefetz | |
| 2006/0036160 A1 | 2/2006 | Altman et al. | |
| 2013/0163728 A1 | 6/2013 | Silberklang et al. | |
| 2014/0323851 A1 | 10/2014 | Barberi et al. | |
| 2015/0276949 A1 * | 10/2015 | Grobshtein | G01T 1/1647 |
| | | | 250/362 |
| 2016/0000794 A1 | 1/2016 | Chiorini et al. | |
| 2016/0022228 A1 * | 1/2016 | Khen | A61B 6/4258 |
| | | | 250/363.05 |
| 2016/0282152 A1 | 9/2016 | Khen et al. | |

* cited by examiner

*Primary Examiner* — Marcus Taningco
(74) *Attorney, Agent, or Firm* — Dean D. Small; The Small Patent Law Group, LLC

(57) ABSTRACT

Nuclear medicine (NM) imaging system includes a detector assembly coupled to a gantry. The NM imaging system also includes a positioning sub-system having a motion controller and a detector motor. The positioning sub-system also includes a proximity sensor device (PSD) coupled to a detector head of the detector assembly. The PSD is configured to be activated. In response to being activated, the PSD is configured to transmit an output signal to stop the detector motor from moving the detector head toward the object. The NM imaging system also includes a secondary circuit that, in response to the PSD being activated, is configured to determine whether the detector head has stopped moving toward the object and, if the detector head has not stopped moving toward the object, is configured to disable the detector motor.

20 Claims, 18 Drawing Sheets

NUCLEAR MEDICINE IMAGING SYSTEMS AND METHODS HAVING A SECONDARY MECHANISM FOR CONTROLLING A DETECTOR HEAD

BACKGROUND

The subject matter disclosed herein relates generally to nuclear medicine (NM) imaging systems, and more particularly to NM imaging systems having a mechanism for stopping and/or removing a detector head.

In NM imaging, such as single photon emission computed tomography (SPECT) or positron emission tomography (PET) imaging, radiopharmaceuticals are administered internally to a patient. The radiopharmaceuticals emit radiation that may be captured by an NM imaging system to generate images for diagnostic review. An NM imaging system may be configured as a multi-head system having a number of individual detector assemblies. The detector assemblies include a movable arm that extends radially-inward toward the patient and a detector head that is held by the movable arm. A positioning sub-system of the NM imaging system controls movement of the detector heads in order to acquire images of a designated region-of-interest. More specifically, the detector heads are positioned adjacent to the region-of-interest to detect the emitted radiation. The detector heads may be positioned within a few centimeters from the patient.

The patient is typically confined within a bore of the NM imaging system during the imaging session. After the imaging session, the patient may physically exit the bore or, in some cases, a table holding the patient may be directed out of the bore. Because the detector heads are positioned adjacent to the patient within the bore, it may be desirable to re-position the detector heads so that the patient can exit. The detector heads are typically moved by activating the same motors that position the detector heads relative to the patient for the imaging session. This standard mechanism for moving the detector heads may become unsuitable if, for example, a power failure occurs or the positioning sub-system malfunctions. In such instances, it may be difficult to remove the patient without injuring the patient or damaging the imaging system. Moreover, physically moving the detector heads away from the patient may be difficult or take a significant amount of time. The patient may become more uncomfortable or upset the longer the patient remains within the bore.

BRIEF DESCRIPTION

In an embodiment, a nuclear medicine (NM) imaging system is provided that includes a gantry including a bore that is sized and shaped to receive an object therein. The NM imaging system also includes a detector assembly coupled to the gantry. The detector assembly includes a movable arm and a detector head that is coupled to the movable arm. The detector head is configured to detect radiation emitted from the object within the bore. The NM imaging system also includes a positioning sub-system having a motion controller and a detector motor that is operably coupled to the movable arm of the detector assembly. The motion controller is configured to control the detector motor to move the movable arm and thereby position the detector head relative to the object. The positioning sub-system also includes a proximity sensor device (PSD) coupled to the detector head. The PSD is configured to be activated when the PSD engages the object or when the PSD is within a predetermined distance from the object. In response to being activated, the PSD is configured to transmit an output signal to the motion controller or to the detector motor that is configured to stop the detector motor from moving the detector head toward the object. The NM imaging system also includes a secondary circuit that, in response to the PSD being activated, is configured to determine whether the detector head has stopped moving toward the object and, in response to determining that the detector head has not stopped moving toward the object, is configured to disable the detector motor.

In some aspects, the secondary circuit is configured to disable the detector motor by at least one of (a) disconnecting the detector motor from an electrical power source or (b) changing the detector motor from an active state to an inactive state. Optionally, the secondary circuit includes non-programmable circuitry or non-reprogrammable circuitry.

Optionally, the detector head is configured to move relative to a base support. The NM imaging system may also include a retracting sub-system that includes an elongated element joining the base support and the detector assembly. The retracting sub-system may be configured to apply a retraction force to the movable arm in a direction toward the base support as the detector head moves from the base support toward the object. The retraction force is configured to pull the movable arm toward the base support after the detector motor is disabled by the secondary circuit. The detector motor is configured to permit the movable arm to be pulled toward the base support after the detector motor is disabled by the secondary circuit.

In some aspects, the motion controller of the positioning sub-system includes a processor and a storage medium that is configured to store programmed instructions accessible by the processor. Responsive to execution of the programmed instructions and receiving the output signal, the processor is configured to transmit a command signal to the detector motor to stop the detector motor from moving the detector head toward the object. The secondary circuit is separate and distinct from the motion controller and includes non-programmable circuitry or non-reprogrammable circuitry.

In some aspects, the secondary circuit is configured to determine whether the detector head has stopped moving toward the object within a designated window. The designated window may be a function of at least one of distance or time and may begin upon activation of the PSD. Upon determining that the detector head has not stopped moving toward the object within the designated window, the secondary circuit is configured to disable the detector motor. Optionally, the secondary circuit includes a delay circuit that is configured to disconnect the detector motor from an electrical power source upon determining that the detector head has not stopped moving toward the object within the designated window. The delay circuit is configured to be deactivated if the detector head stops moving toward the object within the designated window.

In some aspects, the NM imaging system also includes a retracting sub-system that is distinct from the positioning sub-system. The retracting sub-system may be operably coupled to the detector assembly. The retracting sub-system may enable movement of the detector head away from the object.

Optionally, the retracting sub-system is devoid of an electrical power source for moving the detector head. The retracting sub-system may include a release trigger and a biasing element that is operably coupled to the release trigger. The release trigger, when activated, may be configured to cause the biasing element to move from a first state to a second state. The biasing element is configured to drive the detector head away from the object when the biasing element moves from the first state to the second state.

Optionally, the retracting sub-system is devoid of an electrical power source for moving the detector head. The retracting sub-system includes a rotary tool and a link assembly that extends between and operably couples the detector head and the rotary tool. The rotary tool may be configured to be moved by an operator. The rotary tool may be operably coupled to the detector head such that the rotary tool causes the detector head to move away from the object within the bore when activated by the operator.

In some aspects, the detector motor is powered by an electrical power source. The secondary circuit is configured to disable the detector motor by disconnecting the detector motor from the electrical power source.

In some aspects, the detector motor is configured to move the detector head during an active state. The secondary circuit is configured to disable the detector motor by changing the detector motor to an inactive state after determining that the detector head has not stopped moving toward the object.

In an embodiment, a nuclear medicine (NM) imaging system is provided that includes a gantry including a bore that is sized and shaped to receive an object therein. The NM imaging system also includes a detector assembly coupled to the gantry. The detector assembly includes a movable arm and a detector head that is coupled to the movable arm. The detector head is configured to detect radiation emitted from the object within the bore. The NM imaging system also includes a positioning sub-system having a motion controller and a detector motor that is operably coupled to the movable arm of the detector assembly. The motion controller is configured to control the detector motor to position the detector head relative to the object. The NM imaging system also includes a retracting sub-system that is operably coupled to the detector assembly. The retracting sub-system is distinct from the positioning sub-system and is configured to enable movement of the detector head away from the object within the bore.

In some aspects, the retracting sub-system includes a release trigger and a biasing element that is operably coupled to the release trigger. The release trigger, when activated, is configured to cause the biasing element to move from a first state to a second state. The biasing element is configured to drive the detector head away from the object within the bore when the biasing element moves from the first state to the second state.

Optionally, the biasing element includes a spring. The spring may be compressed or stretched when the biasing element is in the first state such that a potential energy exists within the biasing element for moving the biasing element to the second state after the release trigger is activated. Optionally, the release trigger is positioned within the bore or proximate to an entrance to the bore.

In some aspects, the retracting sub-system includes a rotary tool and a link assembly that extends between and operably couples the detector head and the rotary tool. The rotary tool may be operably coupled to the detector head such that the rotary tool causes the detector head to move away from the object within the bore when activated.

In some aspects, the retracting sub-system is devoid of an electrical power source for moving the detector head.

In some aspects, the positioning sub-system includes a proximity sensor detector (PSD) coupled to detector head. The PSD is configured to be activated when the PSD engages the object or when the PSD is within a predetermined distance from the object. The positioning sub-system is configured to automatically stop movement of the detector head when the PSD of the respective detector head is activated. Optionally, a secondary circuit is communicatively coupled to the PSD. Responsive to one or more of the PSDs being activated, the secondary circuit is configured to determine whether the detector head of the activated PSD has stopped moving toward the object and, in response to determining that the detector head has not stopped moving toward the object, the secondary circuit is configured to disable the detector motor that moves the detector head of the activated PSD.

In an embodiment, a method is provided that includes positioning an object within a bore of a nuclear medicine (NM) imaging system. The NM imaging system includes a detector assembly having a movable arm and a detector head coupled to the movable arm. The detector head is configured to detect radiation emitted from the object within the bore. The method also includes controlling a detector motor that is operably coupled to the movable arm of the detector assembly to position the detector head relative to the object and determining that the detector head has engaged the object within the bore or is within a predetermined distance from the object. In response to determining that the detector head has engaged the object or is within the predetermined distance from the object, the method also includes transmitting an output signal to stop the detector head moving toward the object. In response to determining that the detector head has not stopped moving toward the object following transmittance of the output signal, the method also includes disabling the detector motor using a secondary circuit of the NM imaging system.

In some aspects, the detector motor is powered by an electrical power source and, in response to determining that the detector head has not stopped moving toward the object, the secondary circuit is configured to disable the detector motor by at least one of disconnecting the detector motor from the electrical power source or changing a state of the detector motor from an active state to an inactive state.

DETAILED DESCRIPTION

Figure 1:
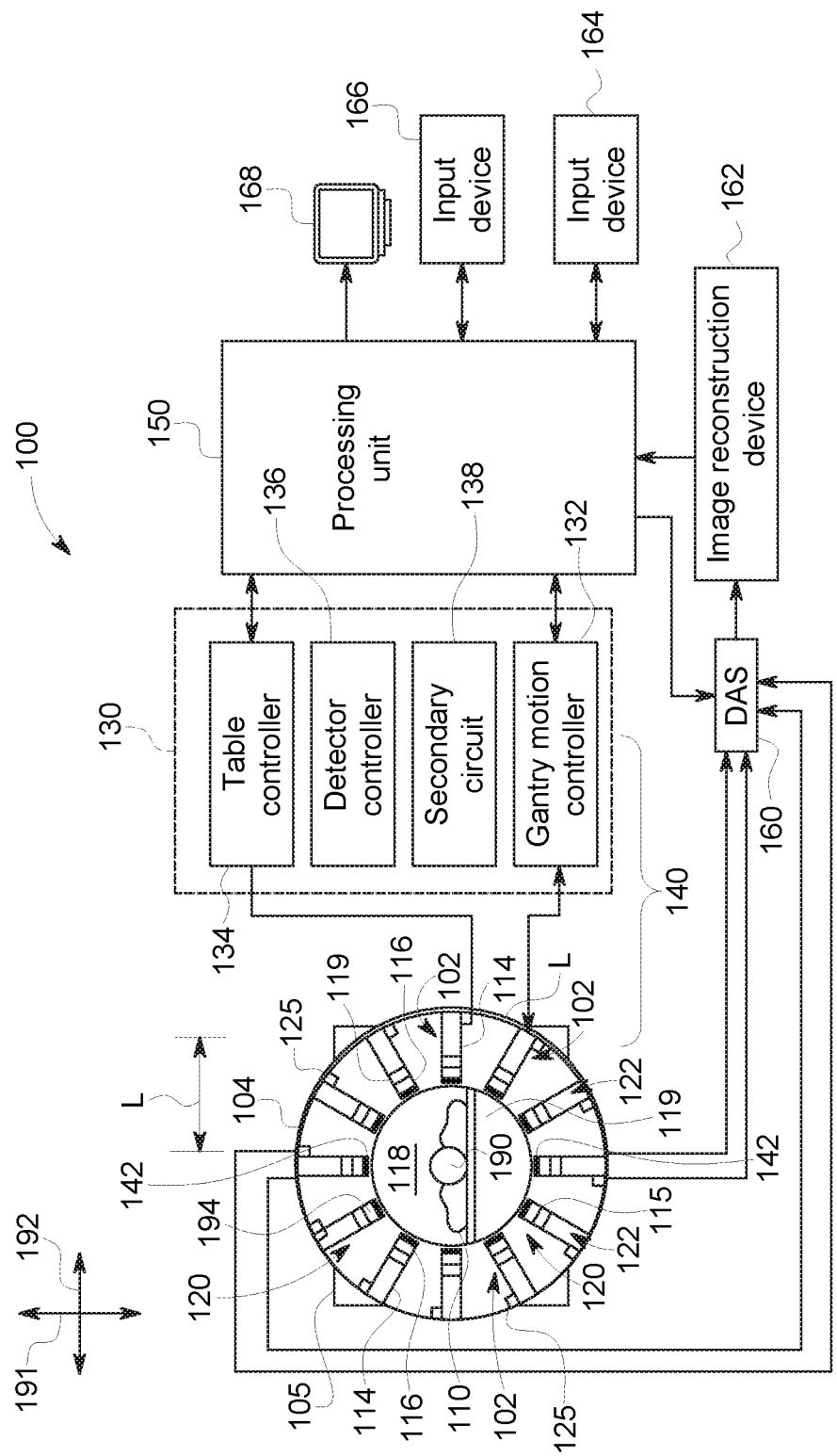
FIG. 1 provides a schematic view of a nuclear medicine (NM) imaging system in accordance with an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings.

As used herein, phrases such as "a plurality of [elements]" and the like, when used in the description and claims, do not necessarily refer to each and every element that a system may have. The system may have other elements that are similar to the plurality of elements but do not have the same features or limitations. For example, the phrase "a plurality of detector assemblies [being/having a recited feature or limitation]" does not necessarily mean that each and every detector assembly of the system has the recited feature or limitation. Other detector assemblies may not include the recited feature or limitation. Similarly, phrases such as "each of the detector assemblies [being/having a recited feature or limitation]" and the like, when used in the description and claims, does not preclude the possibility that the system may have other detector assemblies. Unless explicitly stated otherwise (e.g., "each and every detector assembly of the NM imaging system"), embodiments may include similar elements that do not have the recited features or limitations. As used herein, the phrase "configured to [accomplish a designated function or be used in a designated manner]" means the element is intentionally designed or constructed to accomplish the designated function or to be used in the designated manner.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Embodiments set forth herein include nuclear medicine (NM) imaging systems, methods of acquiring NM images, and computer readable media having one or more software modules that direct one or more processors to execute the methods described herein. Embodiments described herein and illustrated by the figures may be implemented in imaging systems, such as, for example, single photon emission computed tomography (SPECT), SPECT computed tomography (SPECT-CT), positron emission tomography (PET), and PET-CT.

A technical effect of at least one embodiment includes automatically stopping movement of a detector head toward an object within a bore of the NM imaging system during an imaging session. Optionally, the embodiment may automatically retract or withdraw the detector head. A technical effect of at least one embodiment includes the ability to retract a detector head when the detector head is incapable of being moved using the designed mechanism for moving the detector head. For example, the NM imaging system may have a positioning sub-system that controls a motor for positioning the detector head during an imaging session. After a power failure or a malfunction of the NM imaging system, the positioning sub-system may be incapable of retracting the detector head. At least one embodiment allows retraction of the detector head through a different mechanism.

The NM imaging system includes a plurality of detector heads (e.g., 4, 5, 6, 7, 8, 9, 10, 11, 12 or more) that are positioned about a bore of the NM imaging system. The detector heads may be selectively positioned. For example, the detector heads may be moved along unique paths for positioning the plurality of detector heads about a region-of-interest (ROI) of an object. The detector heads may be moved by respective motors. At least some of the detector heads may be movable in an axial direction (e.g., generally toward or away from a longitudinal axis extending through the bore) and rotatable about a respective unit axis that extends parallel to the longitudinal axis. The detector heads may also be moved as a group. For example, a set of detector heads may be rotated as a group about the longitudinal axis. In some embodiments, only a select number of the detector heads (e.g., 3, 4, 5, 6, or 7 detectors units) may be used to obtain the persistence images. For example, embodiments may move the detector heads closer to or away from the bore and rotate the detector heads about the respective unit axes such that the detector heads generally oppose each other across the bore with the object therebetween. The detector heads may have respective detector field-of-views (FOVs).

The detector heads may be moved toward or away from the object within the bore. Optionally, the detector heads are rotatable about axes that extend parallel to the bore. For example, a central longitudinal axis may extend through a geometric center of the bore. The detector heads may be distributed about the bore and face the bore. The detector heads may be moved generally toward or generally away from the central axis. The detector heads may also be rotatable about a detector axis that is parallel to the central axis.

FIG. 1 provides a schematic view of a nuclear medicine (NM) imaging system 100 in accordance with various embodiments. Generally, the imaging system 100 is configured to acquire imaging information (e.g., photon counts) from an object to be imaged (e.g., a human patient) that has been administered a radiopharmaceutical.

It should be noted that the arrangement of FIG. 1 is provided by way of example for illustrative purposes, and that other arrangements may be employed in various embodiments. In the illustrated example, the NM imaging system 100 includes a plurality of detector assemblies 102 that are coupled (e.g., mounted) to a gantry or rotor 104 that includes a bore 118 of the NM imaging system 100. The bore 118 is sized and shaped to receive an object 110 therein. The imaging system 100 may also include a table 119 that is positioned within the bore 118. The table 119 is configured to support the object 110, such as a patient. The detector assemblies 102 are positioned circumferentially about the bore 118. The detector assemblies 102 may be positioned within the gantry 104 such that the detector assemblies 102 are not visible to the patient or, alternatively, at least a portion of the detector assemblies 102 may be exposed within the bore 118. A central longitudinal axis 190 extends through a center of the bore 118.

The imaging system 100 typically includes a plurality of the detector assemblies 102, although it is contemplated, in some embodiments, that the imaging system 100 only includes a single detector assembly. In the illustrated embodiment, each detector assembly 102 includes a movable arm (or radial beam) 114 and a detector head 116 that is coupled to the movable arm 114. The detector head 116 is configured to detect radiation emitted from the object 110 within the bore 118. The detector head 116 is disposed at a radially-inward end or distal end 115 of the movable arm 114. The movable arm 114 is configured to move the detector head 116 axially toward and/or away from a center of the bore 118 (and/or in other directions). To this end, the movable arm 114 may move linearly between a fully retracted position and a fully extended position. Optionally, the detector head 116 is rotatable about a unit axis 194 that is parallel to the central longitudinal axis 190. Optionally, the gantry 104 is rotatable about the central longitudinal axis 190. Although the detector heads 116 of the illustrated embodiment are configured to (a) move toward or away from the bore 118 in a linear manner; (b) rotate about the unit axis 194; and (c) collectively rotate about the central longitudinal axis 190, it is contemplated that the detector head 116 may be movable in other manners.

Each detector head 116 may have a relative position with respect to the bore 118 or a relative position with respect to the object 110. The relative position may include a spatial location (e.g., coordinates in an X, Y, Z space or a vector), a group rotational position (e.g., rotational position of the gantry 104 about the central longitudinal axis 190), and an individual rotational position (e.g., rotational position about the unit axis 194). In some embodiments, the relative position of each detector head 116 may be defined by a length of the movable arm 114, a rotational position of the gantry 104 (e.g., number of degrees relative to a known position), and a rotational position of the detector head 116 (e.g., number of degrees relative to a known position). Embodiments may determine a location of the object 110 within the bore 118 and determine a desired position of each detector head 116 for imaging the ROI of the object 110.

To this end, the imaging system 100 and/or the detector heads 116 may include encoders (not shown) that identify the length of the movable arm 114, the rotational position of the gantry 104, and the rotational positions of the detector heads 116. For example, each of the movable arms 114 may be operably coupled to one or more detector motors 125 that selectively controls the extension of the movable arm 114. When the detector motor 125 moves the movable arm 114, an encoder may determine a length of the movable arm 114 based on a state of the detector motor 125 (e.g., number of revolutions of a lead screw) and/or a state of the movable arm 114. Similarly, an encoder may be operably coupled to the gantry 104 and determine a rotational position of the gantry 104 relative to a stator 105. Similarly, an encoder may be operably coupled to the detector head 116 and determine a rotational position of detector head 116 relative to a base or home position.

The detector head 116 may be, for example, a semiconductor detector. For example, a semiconductor detector in various embodiments may be constructed using different materials, such as semiconductor materials, including Cadmium Zinc Telluride (CdZnTe), often referred to as CZT, Cadmium Telluride (CdTe), and Silicon (Si), among others. The detector head 116 may be particularly configured for use with, for example, nuclear medicine (NM) imaging systems, positron emission tomography (PET) imaging systems, and/or single photon emission computed tomography (SPECT) imaging systems.

Each of the detector heads 116 in various embodiments is smaller than a conventional whole body or general purpose imaging detector. A conventional imaging detector may be large enough to image most or all of a width or length of a patient's body at one time and may have a diameter or a larger dimension of approximately 50 cm or more. In contrast, each of the detector heads 116 may have dimensions of, for example, 4×28 cm and may be formed of Cadmium Zinc Telluride (CZT) tiles or modules. As another example, each of the detector heads 116 may be 8×8 cm in size and be composed of a plurality of CZT pixelated modules (not shown). For example, each module may be 4×4 cm in size and have 16×16=256 pixels (pixelated anodes). In some embodiments, each detector head 116 includes a plurality of modules, such as an array of 1×7 modules. However, different configurations and array sizes are contemplated including, for example, detector heads 116 having multiple rows of modules.

Each of the detector heads 116 has a detector surface or face, which is directed towards the object 110 or an (ROI) within the object 110. It should be understood that the detector heads 116 may be different sizes and/or shapes with respect to each other, such as square, rectangular, circular or other shape. An actual FOV of each of the detector heads 116 may be directly proportional to the size and shape of the respective detector head. The detector heads 116 are arranged in a set or array 120. The set 120 may be rotated as a group about the bore 118 or, more specifically, about the central longitudinal axis 190.

Accordingly, each of the detector heads 116 may be rotated with other detector heads 116 about the central longitudinal axis 190, selectively moved axially toward or away from the central longitudinal axis 190, and selectively rotated about a respective unit axis 194 that extends parallel to the central longitudinal axis 190. As used herein, an element or component is "selectively rotatable," "selectively movable," and the like if the element or component may be controlled in a manner that is different with respect to similar elements or components. For example, one detector head may be rotated 15° and another detector head may be rotated 10°. The phrases do not require, however, the each element or component be controlled differently. Instead, the terms "selective" or "selectively" only acknowledge that the element or component may be controlled differently.

The table 119 is configured with a support mechanism (not shown) to support and carry the object 110 in one or more of a plurality of viewing positions within the bore 118 and relative to the detector heads 116. For example, the table 119 may be operably coupled to one or more motors (not shown). The motors may be configured to move the table 119 along the central longitudinal axis 190, along an elevation axis 191, and also along a lateral axis 192. The axes 190-192 are mutually perpendicular. As such, the table 119 and the corresponding motors may selectively position the object 110 within the bore 118. As described above with respect to the detector heads, an encoder or other device may determine a position of the table 119 within the bore 118.

In the illustrated embodiment, the gantry 104 is circular or donut-shaped. In other embodiments, however, the gantry 104 may be configured to have other shapes. For example, the gantry 104 may be formed as a closed ring or circle, or as an open arc or arch which allows the object 110 to be easily accessed while imaging and facilitates loading and unloading of the object 110. The gantry 104 may be rotated about the central longitudinal axis 190.

Optionally, for embodiments employing one or more parallel-hole collimators, multi-bore collimators may be constructed to be registered with pixels of the detector heads 116, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A control system 130 may control the movement and the positioning of the table 119, the detector heads 116, the gantry 104 and/or other components. The control system 130 may have a gantry motion controller 132, a table motion controller 134, a detector motion controller 136, and a secondary circuit 138. The motion controllers 132, 134, 136 may be automatically commanded by a system processor (or processing unit) 150, manually controlled by an operator, or a combination thereof. As described herein, the secondary circuit 138 is configured to operate when other mechanisms for moving the detector heads 116 are malfunctioning and/or inoperable. Optionally, the secondary circuit 138 may include elements that are separate and distinct from the motion controllers 132, 134, and 136 and, optionally, the processing unit 150. For example, the secondary circuit 138 may include hardwired circuitry that is separate and distinct from the motion controllers 132, 134, and 136 and, optionally, the processing unit 150. More specifically, the hardwired circuitry may not be used by the motion controllers or the processing unit.

The gantry motion controller 132 is configured to move the detector heads 116 with respect to the object 110. The gantry motion controller 132 may control one or more motors (not shown) to move the detector heads 116 as a group about the central longitudinal axis 190. In some embodiments, the gantry motion controller 132 may cause the gantry 104 to rotate about the axis 190, which may include motion of less than or up to 180°. It is contemplated, however, that the gantry 104 may rotate more than 180°.

The table motion controller 134 may move the table 119 to position the object 110 relative to the detector heads 116. The table 119 may be moved in up-down directions along an elevation axis 191, in-out directions along the central longitudinal axis 190, and lateral directions along the lateral axis 192. The detector motion controller 136 may control movement of each of the detector heads 116 to move together as a group or individually. The detector motion controller 136 also may control movement of the detector heads 116 in some embodiments to move closer to and farther from a surface of the object 110, such as by controlling translating movement of the detector heads 116 linearly towards or away from the object 110 (e.g., sliding or telescoping movement). The detector motion controller 136 may also control the pivoting or rotating movement of the detector heads 116. For example, one or more of the detector heads 116 may be rotated about the unit axis 194 to view the object 110 from a plurality of angular orientations.

It should be noted that motion of one or more detector heads 116 may be in directions other than strictly axially or radially, and motions in several motion directions may be used in various embodiment. The term "motion controller" may be used to indicate a collective name for all motion controllers. It should be noted that the various motion controllers may be combined, for example, the detector motion controller 136, the table motion controller 134, and the gantry motion controller 132 may be combined to position the detector heads 116 relative to the object for imaging the object. One or more of the motion controllers may have a processor and a storage medium (e.g., memory) that is configured to store programmed instructions accessible by the processor. The processor is configured to execute one or more operations based on the programmed instructions. For example, the processor may transmit command signals to one or more of the motors. Optionally, a collimator of a detector head 116 may be movable. In such embodiments, a collimator motion controller (not shown) may be provided that is configured to control motion of the collimator.

The imaging system 100 also includes a positioning sub-system 140, which may include elements that control positioning of the detector heads 116 relative to the object 110. For example, the positioning sub-system 140 includes the detector motion controller 136 and, optionally, one or more of the other motion controllers. The positioning sub-system 140 also includes one or more of the motors 125. Optionally, the positioning sub-system 140 includes one or more of the motors that controls positioning of the table 119 and the gantry 104. The motion controller 136 is configured to control the detector motor 125 to position the detector head 116 for detecting radiation emitted from the object 110.

Optionally, the positioning sub-system 140 also includes a proximity sensor device (PSD) 142 coupled to a respective detector head 116. The PSD 142 is configured to be activated when the PSD 142 engages the object 110 or when the PSD 142 is within a predetermined distance from the object 110, such as one centimeter or less. In certain embodiments, the PSD 142 is a pressure sensitive device. In response to being activated, the PSD 142 is configured to transmit a command signal to stop the detector head 116 moving toward the object 110. For example, the command signal may be sent to the motion controller 136, which may then transmit a command signal to the detector motor 125 to stop moving toward the object 110. Alternatively, the command signal may be sent directly to the detector motor 125, bypassing the motion controller. Examples of PSDs that may be used in one or more embodiments are described in U.S. Pat. No. 5,486,700 and U.S. Patent Application Publication Nos. 2013/0163728 and 2016/0007941, each of which is incorporated herein by reference in its entirety.

In some embodiments, the secondary circuit 138 is communicatively coupled to the PSDs 142. In response to a PSD 142 being activated, the secondary circuit 138 is configured to determine whether the detector head 116 has stopped moving toward the object 110 and, if the secondary circuit 138 determines that the detector head 116 has not stopped moving toward the object 110, the secondary circuit 138 is configured to disable the detector motor 125 that is associated with the activated PSD 142. For example, the detector motor 125 may be powered by an electrical power source. The secondary circuit 138 may be configured to disable the detector motor 125 by disconnecting the detector motor 125 from the electrical power source. Alternatively or in addition to disconnecting the detector motor 125 from the power source, the secondary circuit 138 may be configured to disable the detector motor 125 by changing a state of the detector motor 125. In some configurations, a motor may only be operational if the motor is in an active state. If a motor is not in an active state or, in other words, in an inactive state, the motor may not be operable or capable of moving a load. Accordingly, in some embodiments, the secondary circuit 138 is configured to change the detector motor 125 associated with the activated PSD 142 to an inactive state after determining that the detector head 116 has not stopped moving toward the object 110. Optionally, the positioning sub-system 140 may stop movement of all other detector heads 116.

As used herein, the phrase "stop movement of the detector head[s] moving toward the object" or "stopping movement of the detector head[s] moving toward the object" and the like includes the detector head changing directions. For example, upon activation of the PSDs 142, the motors 125 may immediately change from driving the detector head 116 toward the object 110 to driving the detector head 116 away from the object 110. In other embodiments, upon activation of the PSDs 142, the motors 125 may stop driving the detector head 116 toward the object 110 for a designated period of time and then begin driving the detector head 116 away from the object 110. Yet in other embodiments, upon activation of the PSDs 142, the motors 125 may cease operating such that the detector head 116 stops moving toward the object 110 and is held in the same position until further commands are provided or until the detector head 116 is physically removed by an individual (e.g., the operator or the patient).

In some embodiments, the detector heads 116 may be may be moved away from the object using a retracting sub-system that is operably coupled to the detector assembly 102. The retracting sub-system may include one or more components that are separate and distinct from the positioning sub-system 140. The retracting sub-system may enable the NM imaging system to move the detector head 116 away from the object 110 within the bore 118. For example, the retracting sub-system may enable an individual to manually remove the detector head 116. Optionally, the retracting sub-system may be devoid of an electrical power source for moving the detector head 116. For example, the forces that remove the detector head 116 may be provided only by the individual or by a mechanism that uses stored energy from a biasing element (e.g., a spring). Alternatively, a motor may be used to withdraw the detector head 116. The motor may be the detector motor 125 or an entirely different motor.

Prior to acquiring an image of the object 110 or a portion of the object 110, the detector heads 116, the gantry 104, and the table 119 may be adjusted, such as to first or initial imaging positions, as well as subsequent imaging positions. The detector heads 116 may each be positioned to image a portion of the object 110. Alternatively, for example in a case of a small size object 110, one or more of the detector heads 116 may not be used to acquire data. Positioning may be accomplished manually by the operator and/or automatically, which may include using, for example, image data such as other images acquired before the current acquisition, such as by another imaging modality such as X-ray Computed Tomography (CT), MM, X-Ray, PET or ultrasound. In some embodiments, the additional information for positioning, such as the other images, may be acquired by the same system, such as in a hybrid system (e.g., a SPECT/CT system). Additionally, the detector heads 116 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the detector heads 116, the gantry 104, and/or the table 119 are positioned, image data may be acquired. The image data may be used to generate, for example, persistence images. After the table 119 (or object 110) is positioned, the detector heads 116, the gantry 104, and/or the table 119 may be positioned to acquire three-dimensional (3D) SPECT images. The image data acquired by each detector head 116 may be combined and reconstructed into a composite image or 3D images in various embodiments.

In various embodiments, a data acquisition system (DAS) 160 receives electrical signal data produced by the detector heads 116 and converts this data into digital signals for subsequent processing. However, in various embodiments, digital signals are generated by the detector heads 116. An image reconstruction device 162 (which may be a processing device or computer) and a data storage device 164 may be provided in addition to the processing unit 150.

It should be noted that one or more functions related to one or more of data acquisition, motion control, data processing and image reconstruction may be accomplished through hardware, software, and/or by shared processing resources, which may be located within or near the imaging system 100, or may be located remotely. Additionally, a user input device 166 (e.g., mouse, keyboard, touchpad, touchscreen, and the like) may be provided to receive user inputs (e.g., control commands), as well as a display 168 for displaying screens to the user. The DAS 160 receives the acquired image data from the detector heads 116 together with the relative positions of the detector heads 116 for reconstruction of images.

In various embodiments, the detector head may include an array of pixelated anodes, and may generate different signals depending on the location of where a photon is absorbed in the volume of the detector under a surface of the detector. The volumes of the detector under the pixelated anodes are defined as voxels (not shown). For each pixelated anode, the detector has a corresponding voxel. The absorption of photons by certain voxels corresponding to particular pixelated anodes results in charges generated that may be counted. The counts may be correlated to particular locations and used to construct an image or a composite image.

Figure 2:
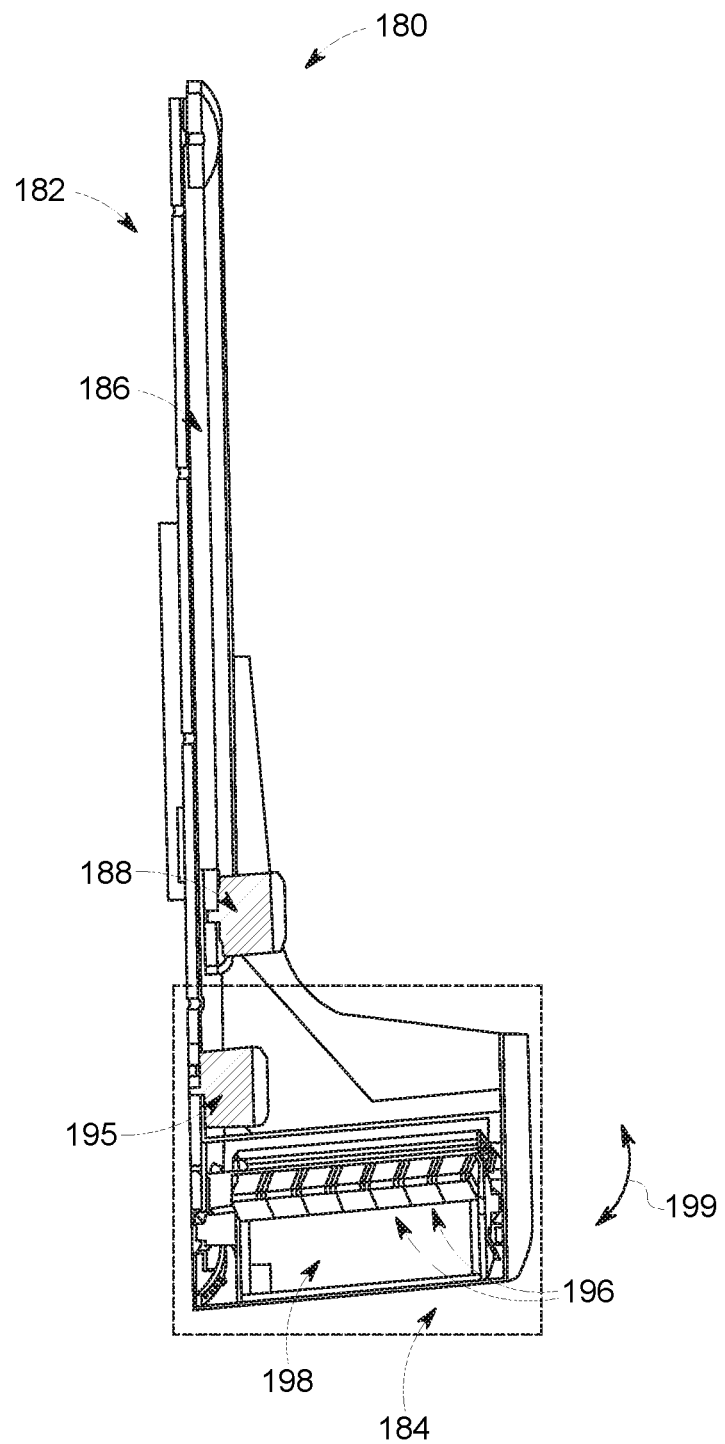
FIG. 2 is a perspective view of a detector assembly in accordance with an embodiment.

FIG. 2 illustrates a detector assembly 180 in accordance with an embodiment. The detector assembly 180 may be used as the detector assembly 102 (FIG. 1) of the imaging system 100 (FIG. 1). The detector assembly 180 includes a movable arm 182 that is configured to couple to a gantry or rotor (not shown), such as the gantry 104, and a detector head 184. The movable arm 182 includes a rail 186 and a detector motor 188. The detector motor 188 may also form part of a positioning sub-system as described herein. The detector motor 188 controls the movement of the detector head 184 by extending or retracting the detector head 184 along the rail 186. In such embodiments, the detector head 184 moves in a linear manner. The movable arm 182 may move telescopically. Optionally, the movable arm 182 and/or the detector head 184 can include covers that allow it to extend and contract as it moves radially in and out.

The detector head 184 includes a sweep motor 195, detector elements 196, and a collimator 198. The detector elements 196 can be CZT modules or other detector element modules discussed throughout for detecting imaging data. Sweep motor 195 controls the rotation angle of the detector head 184 in relation to a unit axis, such as the unit axis 194, or other reference point. A sweep motion 199 of the detector head 184 is shown in FIG. 2. A detector motion controller, such as the controller 136, can provide instruction and control to either or both of the detector motor 188 or the sweep motor 195. Thus, each detector assembly 180 is independently controllable to increase or decrease a length of the detector assembly 180 (or the movable arm 182) and independently controllable for a rotational position of the detector head 184. The detector motor 188 and the sweep motor 195 can be two separate motors. Alternatively, the functionality of the two motors may be provided by one motor.

Figure 3:
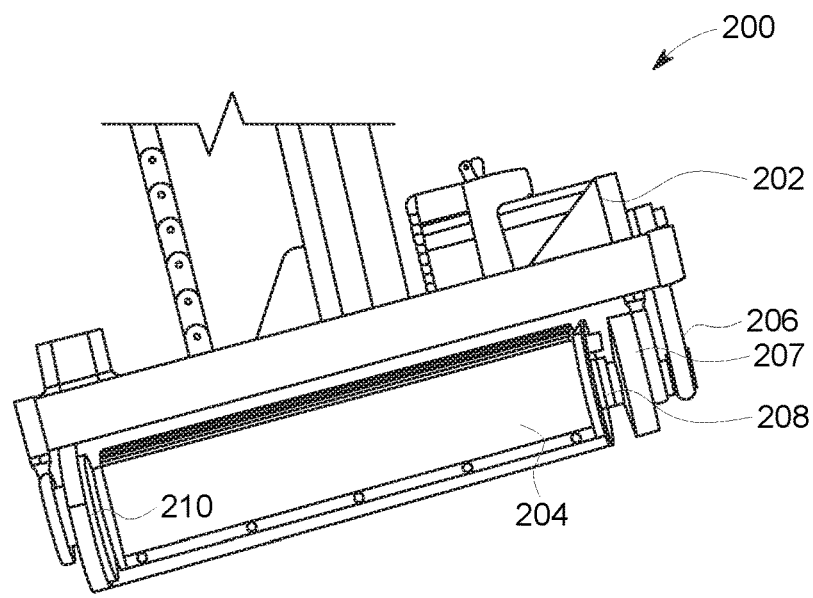
FIG. 3 provides a perspective view of a detector head in accordance with an embodiment.
Figure 4:
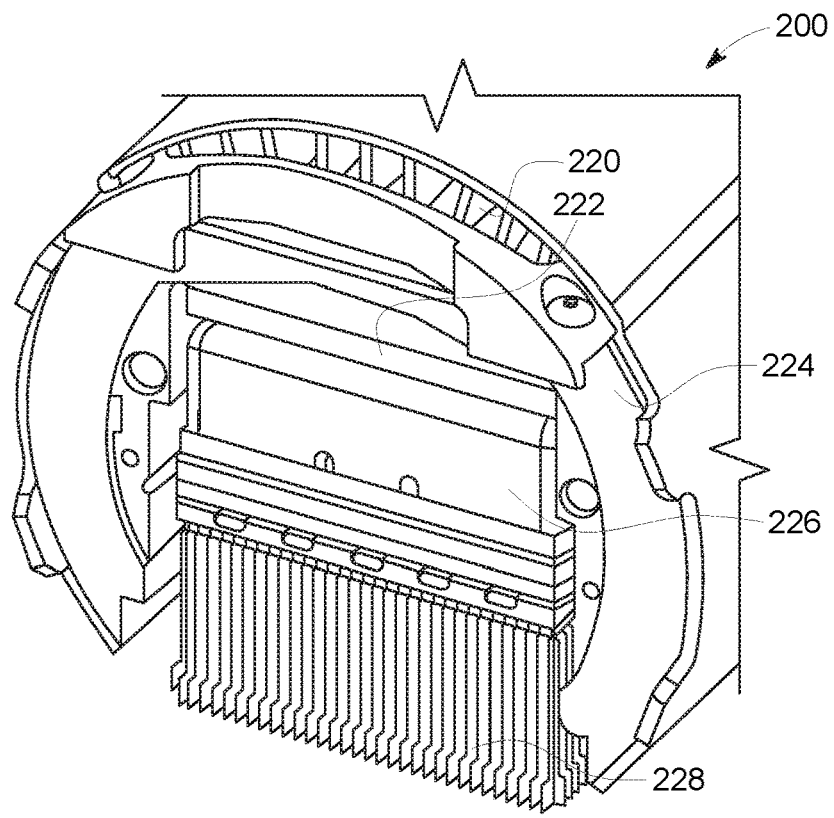
FIG. 4 shows a sectional view of the detector head of FIG. 3.

FIG. 3 is a perspective view of a detector head 200 formed in accordance with various embodiments, and FIG. 4 is a sectional view of the detector head 200. The detector head 200 may be used as part of the detector assembly 102 (FIG. 1) or the detector assembly 180 (FIG. 2). As shown in FIG. 3, the detector head 200 includes a stepper motor 202 that may be utilized to rotate the detector head 200. It may be noted that motors other than stepper motors may be used in various embodiments. Generally, "step-and-shoot" motion may be employed in various embodiments. In step-and-shoot motion, the detector head 200 is rapidly pivoted, and then remains stationary during data collection. Step-and-shoot motion may be utilized in various embodiments to eliminate or reduce power transients and/or other electronic noise associated with activation of electrical motors. Use of step-and-shoot motion may also be utilized to eliminate orientation uncertainties associated with each collected photon.

However, it may be noted that, in various embodiments, with fine orientation encoders, and frequent sampling of the orientation encoders, detector aiming may be associated with each detected photon to sufficient accuracy even if the detectors are continuously pivoting during data acquisition. The detector head 200, for example, may include a shield, a processing board, a detector (e.g., a CZT detector) and a collimator 204. The detector head 200 also includes a gear 206 coupling the stepper motor 202 to the other components, as well as a slip ring 207 (configured to allow for transfer of signals between the rotating components and non-rotating components) and a multiplex board 208. In the illustrated embodiment, the detector head 200 also includes an air channel 210 configured to provide cooling to components of the detector head 200.

Also shown in FIG. 4, the detector head 200 includes a heat sink 220, a printed circuit board 222 (which may incorporate one or more elements of the motion controller or one or more elements of the processing unit), a lead shielding 224, a CZT detector module 226, and a collimator 228 that is registered to the CZT detector module 226 in the illustrated embodiment. Additional details and discussion regarding detector heads is provided in U.S. patent application Ser. No. 14/671,039, entitled "Reduced Airborne Contamination Detector Heads," filed Mar. 27, 2015, the subject matter of which is incorporated herein by reference in its entirety.

Figure 5:
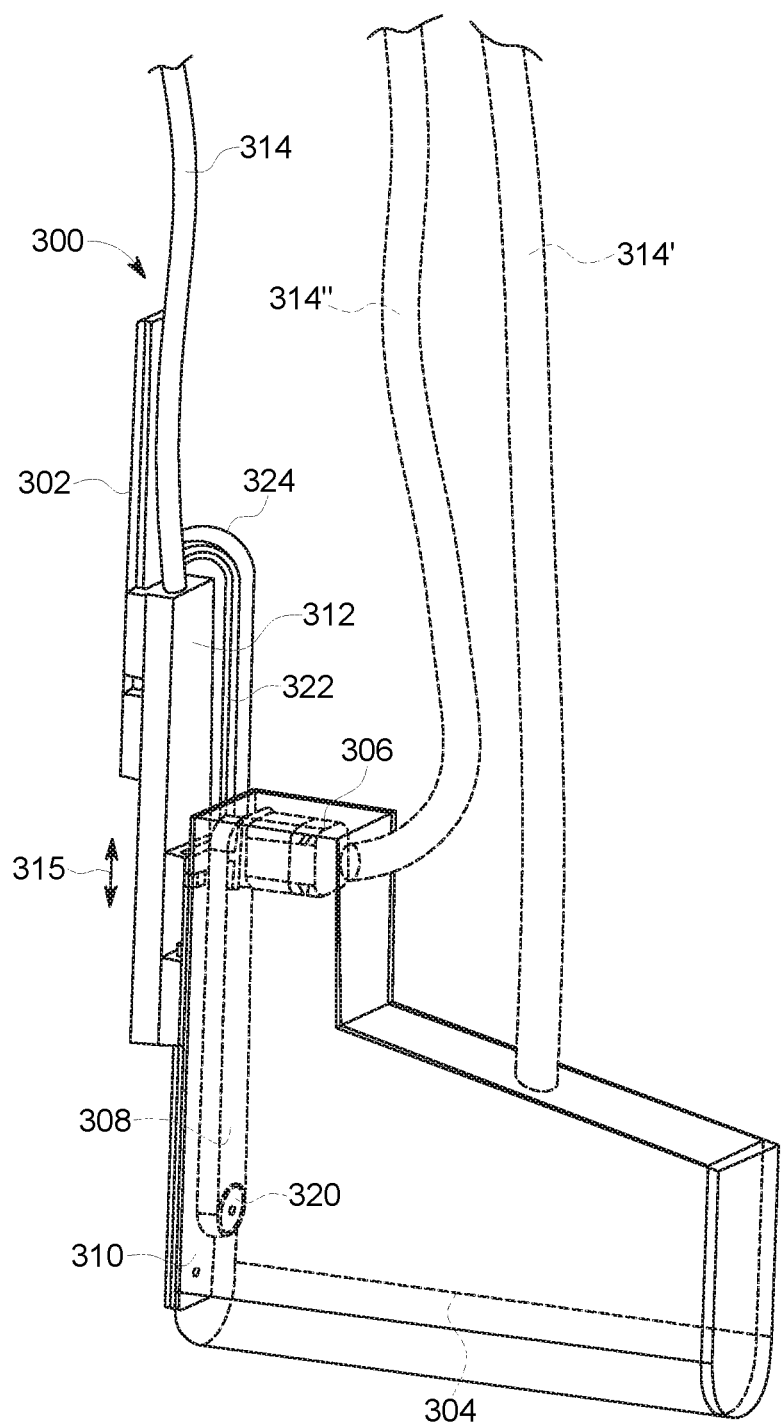
FIG. 5 is a perspective view of a detector assembly in an extended position in accordance with various embodiments.
Figure 6:
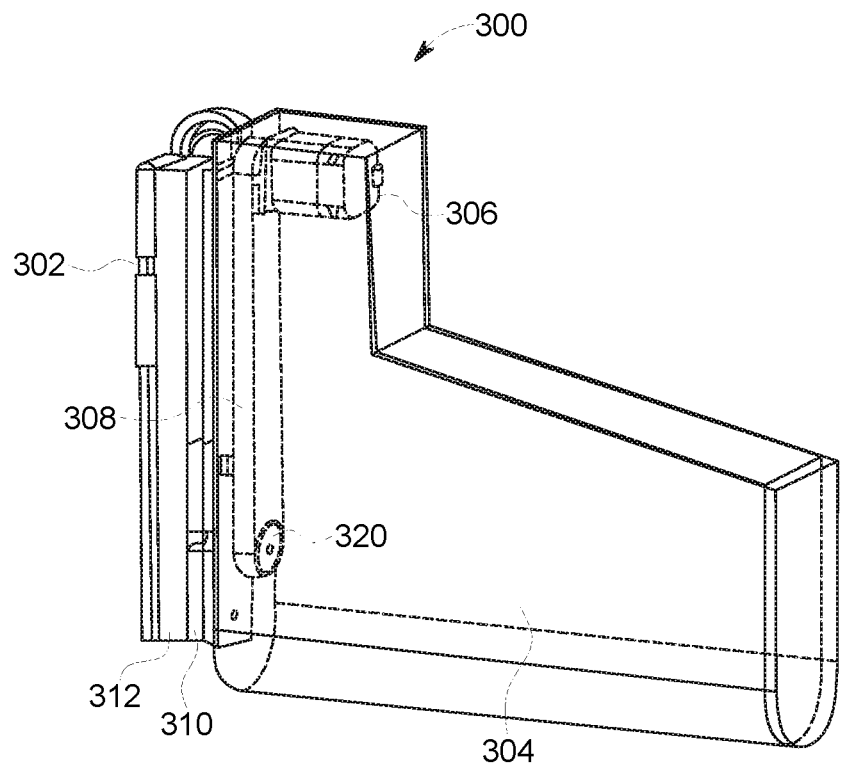
FIG. 6 is a perspective view of the detector assembly of FIG. 5 in a retracted position.

Various embodiments may utilize movable arms that are arranged in telescopic configurations to provide for a desired range of motion in a compact package. FIG. 5 provides a perspective schematic view of a detector assembly 300 in an extended position, and FIG. 6 provides a perspective schematic view of the detector assembly 300 in a retracted position. The detector assembly 300 may include features that are similar or identical to the detector assembly 102 (FIG. 1) and the detector assembly 180 (FIG. 2) and may be used with the imaging system 100 (FIG. 1). As seen in FIGS. 5 and 6, the detector assembly 300 includes an arm base 302, a detector head 304, a detector motor 306, and a detector head belt 308.

Optionally, the detector assembly 300 may be operably coupled to a retracting sub-system, such as the retracting sub-systems described herein. For example, a cable 314 may be coupled to a part of the detector assembly 300. As shown, a proximal end of the cable 314 is coupled to an end of a slider block 312. Alternatively, a proximal end of the cable 314' may be coupled to the detector head 304. In yet another alternative embodiment, the cable 314" may be coupled to the detector motor 306. In some embodiments, the cable may be configured to be pulled in order to retract (directly or indirectly) the detector head. In some embodiments, the cable may be a flexible extension shaft capable of transmitting rotary motion. For example, the cable 314 may be configured to rotate a head gear, and the cable 314" may be configured to rotate the detector motor 306.

The arm base 302 is configured to be fixedly coupled to a gantry, such as the gantry 104 (FIG. 1), having a bore. As used herein, "fixedly coupled" may be understood to mean that the arm base 302 does not move with respect to the gantry when mounted in its intended fashion and an imaging system using the detector assembly 300 is used in its intended fashion. One arm base 302 and one detector assembly 300 are shown in FIGS. 5 and 6; however, it may be noted that plural arm bases 302 may be mounted about the bore of a gantry for which plural corresponding detector heads 304 may be utilized to image an object within the bore.

The detector head 304 includes a carrier section 310 that is slidably coupled to the arm base 302 and configured to be movable along an axial direction 315 in the bore relative to the arm base 302. Thus, the detector head 304 may be articulated radially inwardly (toward the center of the bore) or radially outwardly (away from the center of the bore) to place the detector head 304 in a desired position for imaging. It may be noted that the carrier section 310 and the arm base 302 may be directly or indirectly slidably coupled to each other. For example, in some embodiments, the carrier section 310 and arm base 302 may be directly slidably coupled to each other, for instance, with one of the carrier section 310 or arm base 302 including a guide that slidably accepts a rail of the other. In other embodiments, for increased compactness in the retracted position, the detector assembly 300 may be configured as a telescoping assembly with an intermediate member (e.g., slider block 312) interposed between the arm base 302 and carrier section 310, with the intermediate member slidably coupled to the arm base 302 and carrier section 310 separately, providing an example of an indirect slidable coupling between the arm base 302 and carrier section 310.

As seen in FIG. 5, the detector head 304 may be understood as being distally positioned (e.g., positioned more radially inwardly than the arm base 302). One or more detectors (e.g., one or more CZT detectors), which may be pivoted or tilted within the detector head 304, may be positioned in a distal portion of the detector head 304. It may be noted that the detector head 304 may include one or more shielding members (e.g., for shielding electronics of a detector module from radiation), and may be configured to provide cooling (e.g., by passing a flow of air over cooling fins) to dissipate heat generated by electronics associated with the detectors. The detector head 304 may also include one or more PSDs.

In various embodiments, the detector motor 306 is operably coupled to at least one of the detector head 304 or the arm base 302. In the embodiment depicted in FIGS. 5 and 6, the detector motor 306 is mounted to the carrier section 310 of the detector head 304. Generally, the detector motor 306 is used to drive the detector head belt 308 to articulate the detector head 304 radially (e.g., inwardly toward the center of the bore or outwardly away from the center of the bore). For example, a drive shaft of the detector motor 306 may be rotated to drive the detector head belt 308. The detector motor 306 may also be used to help secure or maintain the detector head belt 308 in a desired position (e.g., by being prevented or inhibited from rotating). It may be noted that, while a motor and belt are used in the depicted embodiment (e.g., detector motor 306 is utilized to drive the detector head belt 308 and to articulate the detector head 304 radially), other devices, systems, or mechanisms may be utilized to articulate the detector head 304 radially in other embodiments.

The depicted detector head belt 308 is operably coupled to the detector motor 306 and to the carrier section 310 of the detector head 304, with rotation of the detector motor 306 (e.g., rotation of a drive or output shaft of the axial motion motor) causing movement of the detector head 304 along the axial direction 315. In the illustrated embodiment, the detector head belt 308 passes around a drive shaft and/or gear of the detector motor 306 and around a detector head gear 320 mounted to the carrier section 310. The depicted detector head gear 320 is mounted to an opposite end of the carrier section 310 than the axial motion motor, with the detector head belt 308 extending along most or all of the length of the carrier section 310 in the axial direction 315.

As mentioned above, for increased compactness in the retracted position, the detector assembly 300 may be configured as a telescoping assembly with an intermediate member (e.g., slider block 312) interposed between the arm base 302 and carrier section 310, with the intermediate member slidably coupled to the arm base 302 and carrier section 310 separately, providing an example of an indirect slidable coupling between the arm base 302 and carrier section 310. As seen in FIG. 5, the detector assembly 300 includes a slider block 312 interposed between the detector head 304 (e.g., the carrier section 310 of the detector head 304) and the arm base 302. The slider block 312 is slidably coupled to the arm base 302 and configured to be moveable in the axial direction 315 with respect to the arm base 302. For example, one of the slider block 312 and arm base 302 may include a guide that accepts a rail of the other. Also, the carrier section 310 of the detector head 304 is slidably coupled to the slider block 312 and configured moveable in the axial direction 315 with respect to the slider block 312. For example, one of the slider block 312 and carrier section 310 may include a guide that accepts a rail of the other.

In various embodiments, one or more belts may be fixed or coupled to the one or more of the arm base 302, slider block 312, or carrier section 310 to articulate the detector head 304 in the axial direction 315, or to articulate the detector assembly 300 between extended and retracted positions.

Figure 7:
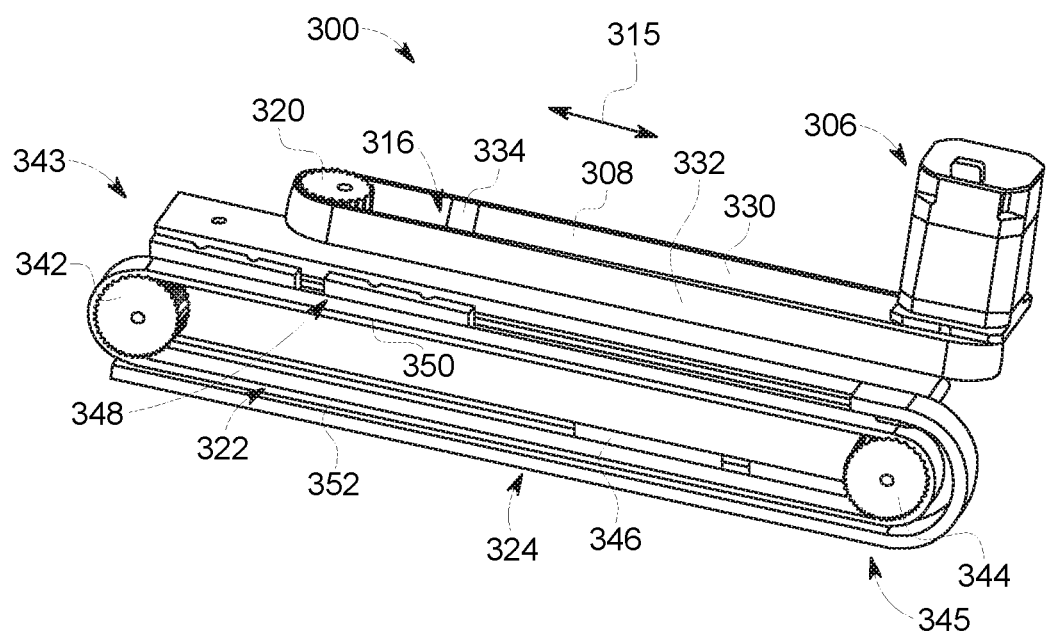
FIG. 7 is a side perspective view of the detector assembly of FIG. 5.

FIG. 7 provides a side perspective view of a portion of the detector assembly 300. The slider block 312 is fixed to the detector head belt 308 at point 316. Accordingly, the slider block 312 moves in the axial direction 315 with the detector belt 308. It may be noted that portion 332 of the detector belt 308, disposed on that opposite side of detector head gear 320 from the portion 330, moves oppositely in or along the axial direction 315 as the slider block 312. The point 316 where the slider block 312 is fixed to the detector head belt 308 may be the location of mounting to a bracket or clip 334 used to fix the slider block 312 to the detector head belt 308.

As also seen in FIG. 7, the detector assembly 300 also includes an idler belt 322. The depicted idler belt 322 is mounted to idler gears 340, 342 disposed on the slider block 312. In the illustrated embodiment, the idler gears 340, 342 are mounted on opposite ends 343, 345, respectively, of the slider block 312. The idler belt 322 is fixed to the carrier section 310 at point 346 (e.g., via a clip or bracket as discussed in connection with point 316) and to the arm base 302 at point 348 (e.g., via a clip or bracket as discussed in connection with point 316). The slider block 312 moves in the axial direction 315 with a portion 350 of the idler belt 322 relative to the arm base 302. Also, the carrier section 310 moves in the axial direction 315 with a portion 352 of the idler belt 322 relative to the slider block 312. With the portion 350 and the portion 352 on opposite sides of the idler gears 340, 342, the arm base 302 and the carrier section 310 move oppositely to each other along the axial direction 315 with respect to the slider block 312. Use of the idler belt 322 thus results in about twice the total movement of the detector head 304 with respect to the arm base 302 for the same motor rotation and/or similar retracted length compared to examples that do not use the idler belt 322 and slider block 312 (see also, e.g., FIG. 3 and related discussion). It may be noted that electrical cables 324 may be disposed about the idler belt 322, with the electrical cables 324 extending along with the detector head 304 to provide electrical communication with the detector head 304 in the various positions at which the detector head 304 may be disposed.

In various embodiments, all or a portion of the arm base 302, detector head 304, and/or slider block 312 may be protected or contained within a cover. The cover may telescope with the detector assembly 300 to provide coverage over a range of motion while still providing compactness in a retracted position.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

Figure 8:
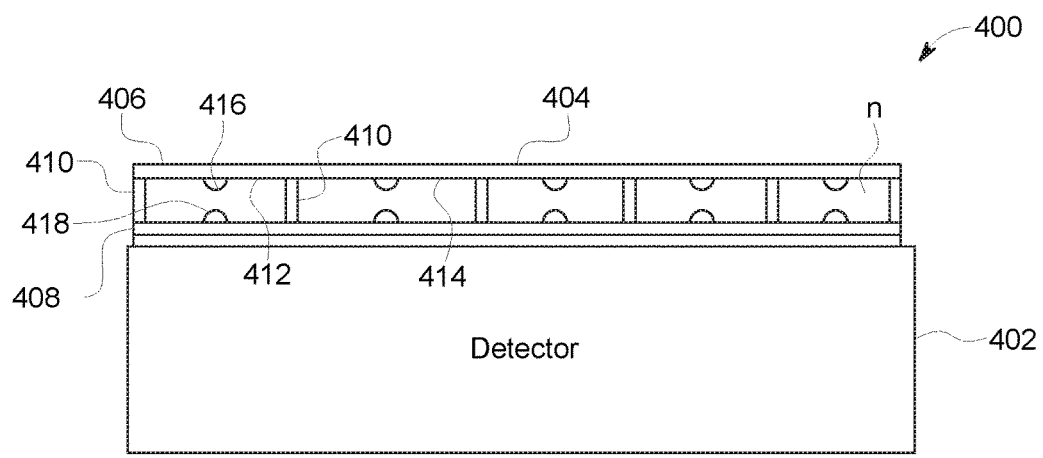
FIG. 8 is a schematic diagram of a proximity sensor device (PSD) that may be used with a detector assembly in accordance with various embodiments.

FIG. 8 is side cross-sectional view of a portion of a PSD 400 that may be incorporated into one or more embodiments described herein. For example, the PSD 400 may be similar or identical to the PSDs 142 (FIG. 1). In the illustrated embodiment, the PSD 400 has a rubber structure that is glued to a detector head 402. There is an array of contacts acting as safety switches. The PSD 400 includes a flexible upper layer 404 having multiple contacts 406. A lower layer 408 may be rigid or flexible.

In some embodiments, the upper layer 404 may be referred to as a sensing plate, and the lower layer 408 may be referred to as a lower pressure sensing plate 408. The PSD 400 also includes a plurality of flexible dividers 410. The flexible dividers 410 are utilized to form separate sensing elements, such as for example, an element 412, and element 414 . . . n, etc. Each element, such as element 412 includes a pair of metallic pads. For example, each element includes a metallic pad 416 that is coupled to a lower surface of the sensing plate 406 and a metallic pad 418 that is coupled to an upper surface of the sensing plate 408.

In operation, when an object or the patient contacts the sensing plate 406, the sensing plate 406 is depressed. Depressing the sensing plate 406 causes the metallic pad 416 to come into physical and electrical contact with the metallic pad 418 to form an electrical circuit. In operation, the electrical circuit outputs a command signal that is utilized by an NM imaging system, such as the imaging system 100 (FIG. 1), to indicate that the PSD 400 has engaged the object. More specifically, the command signal is utilized by the imaging system to stop the detector head 402 moving further toward the object and, optionally, retract the detector head 402. The PSD 400 may be configured to deactivate automatic control of moving parts of the imaging system. For example, when the PSD 400 is activated, the imaging system may stop automatic movement of a gantry, the detector heads, and/or the table.

Figure 9:
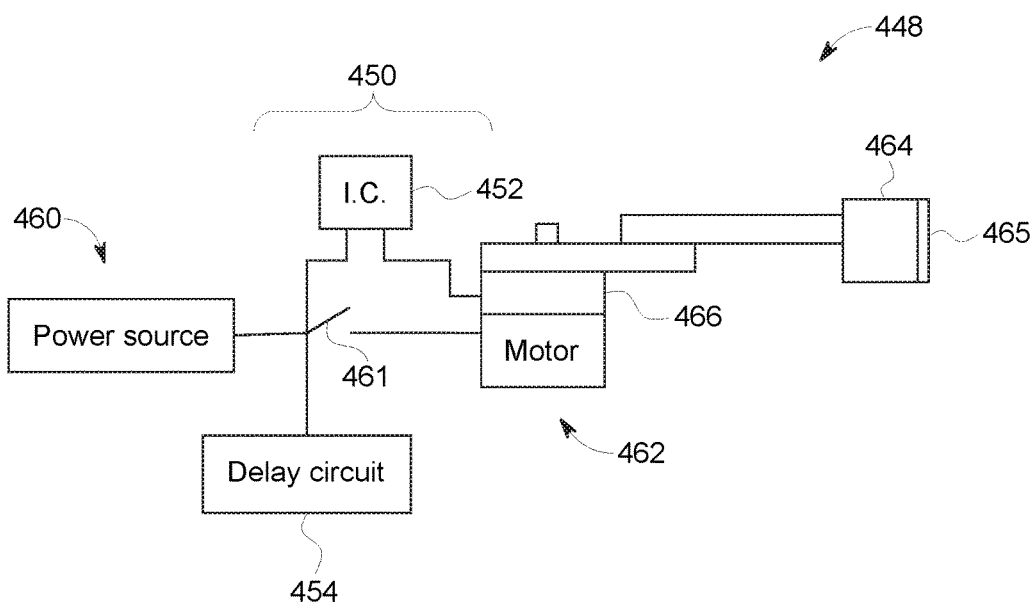
FIG. 9 is a schematic circuit diagram of a secondary circuit in relation to an electrical power source and a motor.

FIG. 9 is a schematic diagram of a portion of a system 448 that includes a secondary circuit 450, an electrical power source 460, and a detector motor 462. The system 448 may be similar or identical to the system 100. The secondary circuit 450 includes an integrated circuit 452 and a delay circuit 454. The integrated circuit 452 may be, for example, one or more field programmable gate arrays (FPGAs) and/or one or more application specific integrated circuits (ASICs). In some embodiments, the delay circuit 454 is an electric circuit that includes resistors and capacitors (e.g., RC circuit) driven by a voltage or current source. The delay circuit 454 may include hardware and/or be hardwired. The integrated circuit 452 and the delay circuit 454 may cooperate or operate individually to disable the detector motor 462 that controls positioning of a detector head 464, which may be similar to the detector heads described herein. The detector head 464 has a PSD 465 coupled thereto. For example, the integrated circuit 452 and/or the delay circuit 454 may disconnect the detector motor 462 from the electrical power source 460 and/or change a state of the detector motor 462 using a switch 461. As described herein, the motor may have one or more states, including at least one active state (e.g., ON state) in which the motor is capable of driving the movable arm and an inactive state (e.g., OFF state) in which the motor is not capable of driving the movable arm.

Optionally, the system 100 also includes a torque limiter 466, which may also be referred to as an overload clutch in some embodiments. When the torque or load of the detector motor 462 exceeds a designated value, the torque limiter 466 permits a driven component (e.g., motor) to slip relative to a rotating component (e.g., shaft) or decouples the driven component with respect to the load. Non-limiting examples of torque limiters that may be suitable for one or more embodiments include friction torque limiters, zero-backlash (or backlash-free) torque limiters, ball/roller bearing torque limiters, ball detent torque limiters, pneumatic torque limiters, magnetic torque limiters, slip clutches, or shear pins. A torque limiter may be packaged as a shaft coupling or hub.

Figure 10:
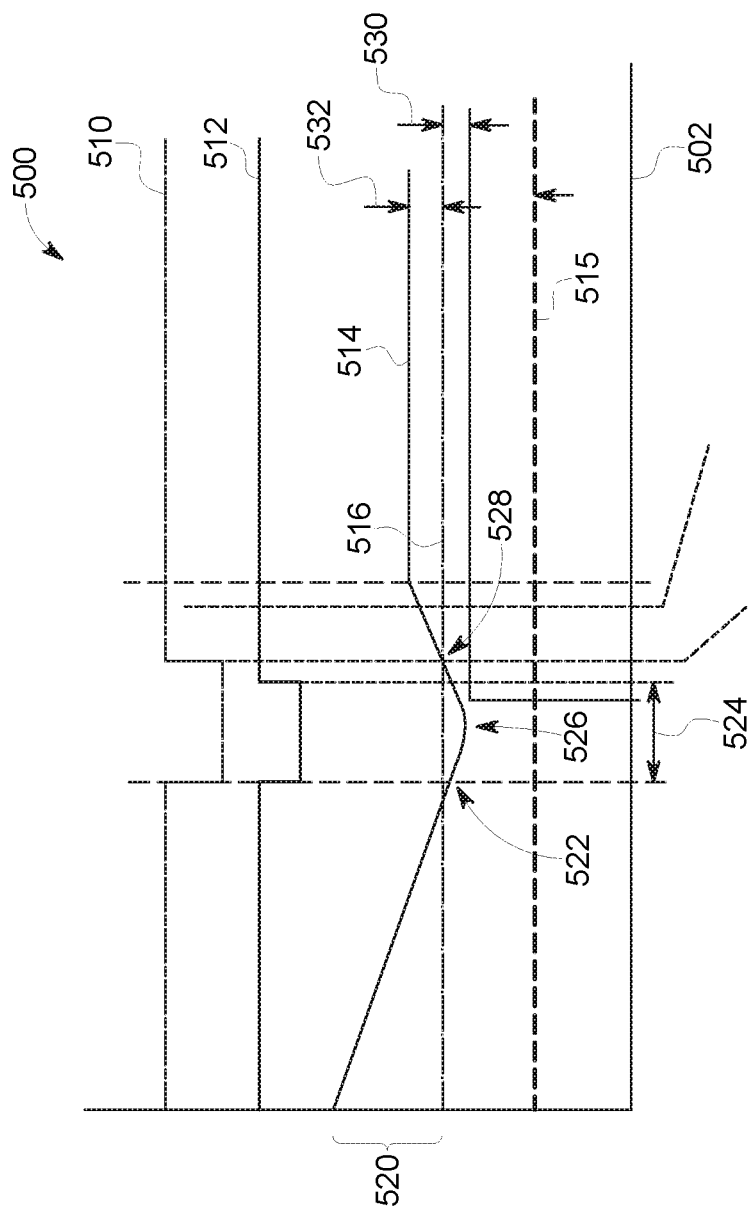
FIG. 10 is a graph illustrating different states of a positioning sub-system in accordance with an embodiment after the PSD is activated.

FIG. 10 is a graph 500 illustrating different states of a positioning sub-system in accordance with an embodiment. In particular, the graph 500 illustrates different states of components of the positioning sub-system during an imaging session in which a PSD is activated and an auto-retract operation is executed by the positioning sub-system. The positioning sub-system may be similar or identical to the positioning sub-system 140 (FIG. 1). The graph 500 includes a horizontal axis 502 for time in which time increases as the axis 502 extends in a left-to-right direction. Elements of the positioning sub-system are represented by different lines within the graph 500. The elements may have different states during operation. The elements include a PSD (represented by line 510), an integrated circuit (represented by line 512), a detector head (represented by line 514), and a motor (represented by line 510). An object (e.g., patient) is also represented by a line 516. Hereinafter, the components will be referred to by their respective lines (e.g., PSD 510, integrated circuit 512, detector head 514, detector motor 515, and patient 516).

As the detector head 514 moves toward the object 516, a separation distance 520 between the detector head 514 and the object 516 decreases. At point 522, the PSD 510 engages the object 516 thereby activating the PSD 510. The PSD 510 transmits a signal to the motion controller (not shown) indicating that the PSD 510 has engaged the object 516. In some embodiments, the motion controller has stored programmed instructions (e.g., software modules) that cause a processor of the motion controller to respond to the signal from the PSD 510. The motion controller transmits a command signal to the detector motor 515 with a command to switch directions of movement so that the detector head 514 is retracted.

In the illustrated embodiment, the integrated circuit 512 is configured to generate a designated window 524 upon activation of the PSD 510. In alternative embodiments, the motion controller generates the designated window 524. The designated window 524 is a function of at least one of position or time. The integrated circuit 512 may monitor the detector motor 515 and/or monitor a position of the detector head 514 to determine if the detector head 514 stops moving toward the object within a maximum predetermined distance. The maximum predetermined distance may be, for example, at most 15 mm, at most 10 mm, or at most 5 mm. In particular embodiments, the maximum predetermined distance is at most 3 mm. For example, if the integrated circuit 512 monitors the detector motor 515, the integrated circuit 512 may determine whether the detector motor 515, which drives the detector head 514 at a known speed, stops movement within a predetermined time period. The predetermined time period may be based on the speed of the detector head 514 and the maximum allowable distance of the designated window 524. The speed of the detector head 514 is a function of the speed of the detector motor 515.

If movement of the detector head 514 does not change (e.g., stop or change directions) within the designated window 524, then a secondary circuit may be activated. In FIG. 10, the secondary circuit is not activated because the detector head 524 stopped moving toward the object 516 and began to retract. More specifically, the detector motor 515 changed direction of movement after receiving a command signal from the motion controller. The command signal may be communicated directly by the PSD or communicated by the motion controller. As shown, the detector head 514 is closest to the patient (or is most engaged to the patient) at point 526. After point 526, the detector motor 515 retracts the detector head 514.

A distance traveled by the detector head 514 between the time at which the PSD 510 is activated (or point 522) and the time at which the PSD 510 stops moving toward the object 516 (or into the object 516) at point 526 is the stopping distance 530. When the PSD 510 disengages from the object 516 at point 528, the PSD 510 is deactivated. When the PSD 510 is deactivated, a signal is sent (e.g., by the PSD 510 or by the motion controller The detector motor 515 may continue to move the detector head 514 away from the object 516 for a designated retraction distance after deactivation of the PSD 510.

The designated retraction distance may be referred to as the release distance 532. Movement of the detector head 514 away from the object 516 may be caused by stored programmed instructions of the motion controller, which may command the detector motor 515 to retract the detector head 514 by the release distance. Movement of the detector head 514 may stop at the release distance. At this time, the operator may determine whether to continue with an imaging session. For example, the operator may provide user inputs to the control system 130 to re-calculate a position of the object 516 within the bore using new information provided by the PSD 510. The new information may include the location of the detector head 514 in which the PSD 510 engaged the object 516.

Figure 11:
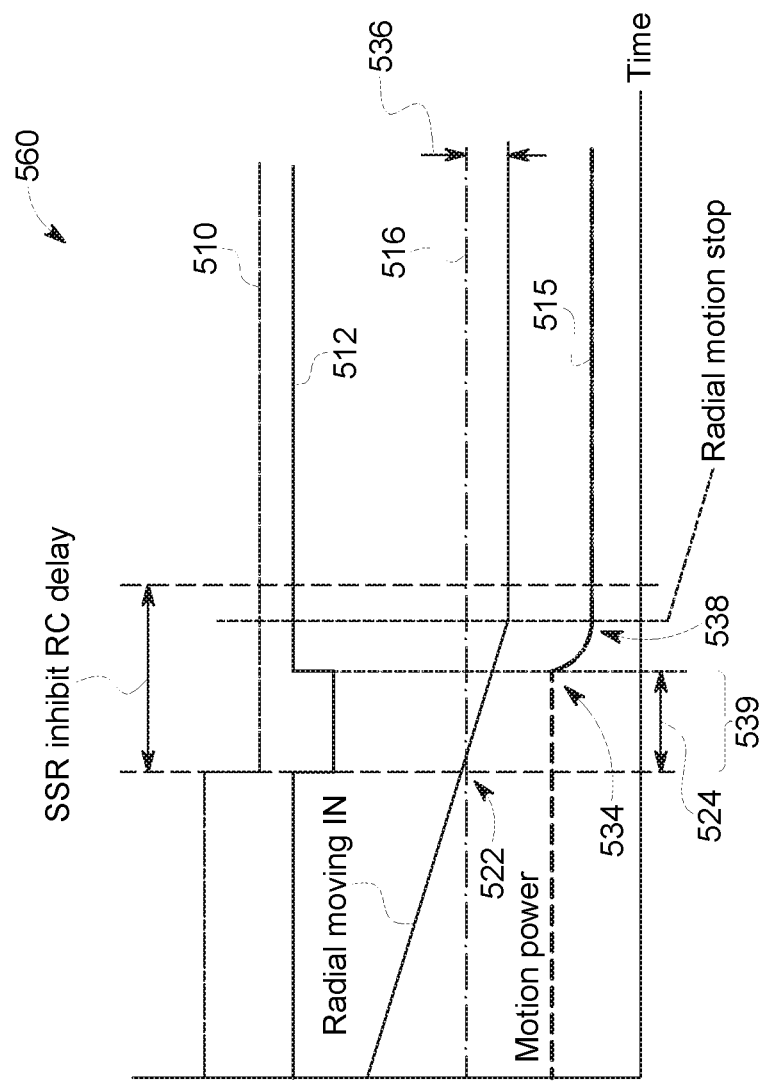
FIG. 11 is a graph illustrating different states of the positioning sub-system during a first failure mode.

FIG. 11 is a graph 540 illustrating different states of the positioning sub-system during a first failure mode. At point 522, the PSD 510 engages the object 516 and transmits a signal to the motion controller. The designated window 524 is generated by the integrated circuit 512. For some reason, however, motion of the detector head 514 did not stop within the designated window 524. In some embodiments, the integrated circuit 512 is configured to inhibit power to the detector motor 515. For example, the integrated circuit 512 may control a switch that disconnects the detector motor 515 with respect to the electrical power source (e.g., the power source 460). The integrated circuit 512 may be configured to inhibit the power within a designated time period 539 from activation of the PSD 510 and/or generation of the designated window 524. For example, the time period 539 may be 30 milliseconds and occur at point 534. The detector motor 515 may stop driving the detector head 514 soon thereafter (e.g., within 15 milliseconds). As shown in FIG. 11, a stopping distance 536 is defined as the distance travelled by the detector head 514 between activation of the PSD 510 and a final stopping point 538 of the detector head 514.

FIG. 11 is a graph 560 illustrating different states of the positioning sub-system during a second failure mode. Again, at point 522, the PSD 510 engages the object 516 and transmits a signal to the motion controller. The designated window 524 is generated by the integrated circuit 512. For some reason, however, motion of the detector head 514 did not stop within the designated window 524. At point 534, the integrated circuit 512 outputs a signal to inhibit power to the detector motor 515. For some reason, however, motion of the detector head 514 did not stop in response to the output signal from the integrated circuit 512.

Figure 12:
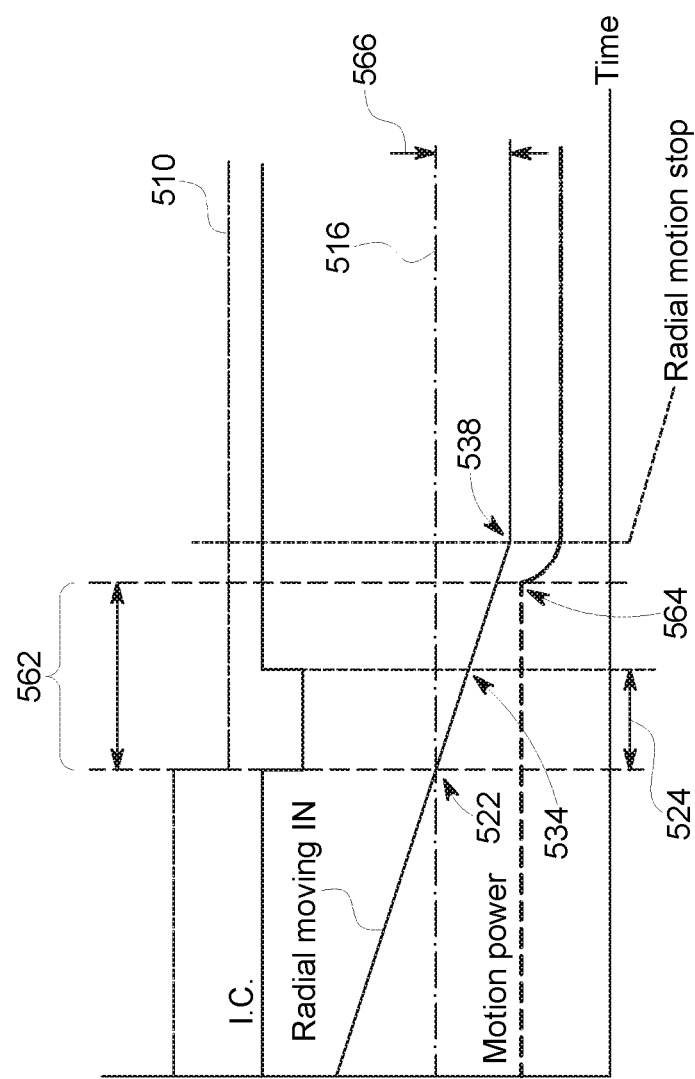
FIG. 12 is a graph illustrating different states of the positioning sub-system during a second failure mode.

In such instances, embodiments may utilize a delay circuit, such as the delay circuit 454. The delay circuit may be configured to inhibit the power within a designated time period 562 from activation of the PSD 510. For example, the time period 562 may be 100 milliseconds and elapse at point 564. The detector motor 515 may stop driving the detector head 514 soon thereafter (e.g., within 15 milliseconds). As shown in FIG. 12, a stopping distance 566 is defined as the distance travelled by the detector head 514 between activation of the PSD 510 and a final stopping point 538 of the detector head 514.

As shown in FIGS. 11 and 12, the final stopping point of the detector head 514 is engaged with the object 516. Due to the relatively quick stoppage of the detector head 514 and/or the PSD 510 allowing some pressing by the object 516, the object 516 is unharmed. As described herein, embodiments may allow the detector assembly to be removed without using the positioning sub-system.

Accordingly, the detector assembly may be retracted using a secondary mechanism if the positioning sub-system fails to retract the detector assembly. The secondary mechanism includes the secondary circuit and one or more mechanical devices (e.g., springs, motors) for retracting the detector assembly. The mechanical devices may be devices that are also used by the positioning sub-system. Alternatively, the mechanical devices may be devices that are not used by the positioning sub-system or are exclusively used by the secondary mechanism.

In some embodiments, the secondary circuit is less vulnerable or susceptible to malware, viruses, or bugs. For instance, the secondary circuit may include firmware and/or hardware (e.g., hard-wired circuitry) that initiates retraction of the detector assembly without relying upon software. For some embodiments, the secondary circuit (or, more specifically, the delay circuit) cannot be re-programmed, hacked, or infected by a malware or viruses. The secondary circuit may be characterized as a non-programmable circuit or logic device having discrete components (e.g., resistors, capacitors, and fixed-function logic gates, such as diodes or transistors) or a non-reprogrammable circuit or logic device (e.g., programmable read-only memory (PROM) or field programmable read-only memory (FPROM) or one-time programmable non-volatile memory (OTP NVM)) in some embodiments. Yet in alternative embodiments, the secondary circuit may include a microprocessor.

One or more embodiments may include a dedicated non-programmable delay circuit or a non-reprogrammable delay circuit that is operably coupled to the PSD. The delay circuit may be configured to effectively disable the detector motor if the detector assembly continues moving toward the patient and, optionally, does not retract. The detector assembly may be determined to be moving toward the patient if, for example, at least one of the following occurs: (1) the PSD is continuously activated for at least designated time period; (2) the detector motor continues to operate for at least a designated time period, or (3) the detector head continues to move toward the patient for at least a designated time period. The secondary circuit may be configured to disable the detector motor by at least one of (a) disconnecting the detector motor from the electrical power source or (b) changing an operating state of the detector motor. In particular embodiments, the delay circuit opens a switch thereby cutting power off to the detector motor.

Figure 13:
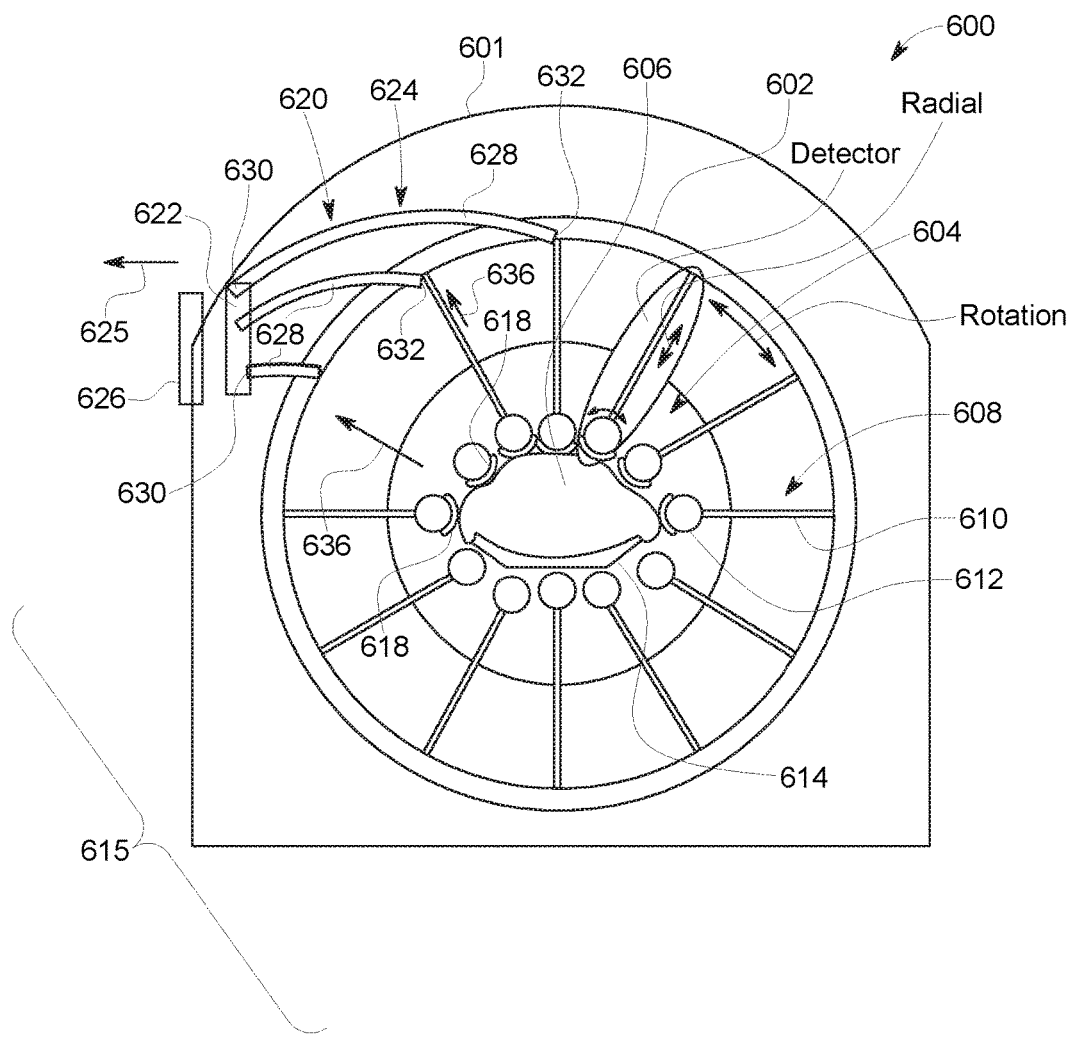
FIG. 13 is a schematic end view of an NM imaging system that includes a retracting sub-system in accordance with an embodiment.

FIG. 13 is a schematic end view of an NM imaging system 600 in accordance with an embodiment. The NM imaging system 600 may be similar to or identical to the NM imaging system 100 (FIG. 1). For example, the NM imaging system 600 may have a positioning sub-system that is configured to automatically retract a detector head when a PSD engages an object. In other embodiments, however, the NM imaging system does not include an automatic retraction process.

As shown, the NM imaging system 600 includes a stator 601 and a gantry 602 that is rotatably coupled to the stator 601. The gantry 602 has a bore 604 that is sized and shaped to receive an object 606 therein. The NM imaging system 600 also includes a set 615 of detector assemblies 608 coupled to the gantry 602. Each of the detector assemblies 608 includes a movable arm 610 and a detector head 612 that is coupled to the movable arm 610. The detector head 612 is configured to detect radiation emitted from the object 606 within the bore 604. Optionally, PSDs 618 are coupled to respective detector heads 612.

The NM imaging system 600 also includes a positioning sub-system (not shown) that is similar or identical to the positioning sub-system 140 (FIG. 1). For example, the positioning sub-system includes a motion controller (not shown) that is operably coupled to the movable arm 610, the detector assembly 608, and a table 614, which holds the object 606. The motion controller is configured to position the table 614 and the detector head 612 relative to one another for detecting the radiation emitted from the object.

The NM imaging system 600 also includes a retracting sub-system 620 that is operably coupled to one or more detector assemblies 608. In the illustrated embodiment, the retracting sub-system 620 is operably coupled to a plurality of the detector assemblies 608 (e.g., a number less than the entire set 615). The retracting sub-system 620 is distinct from the positioning sub-system and allows the NM imaging system 600 to move the detector head 612 away from the object 606 within the bore 604. The retracting sub-system 620 may be configured to use manual power (e.g., power provided by an individual) or stored power (e.g., power provided by a biasing element, such as a spring). After the detector motor is disabled, it may be risky to re-power the detector motor because, prior to the detector motor being disabled, the detector motor was operating improperly. Thus, a manual retraction may be desired. In particular embodiments, the retracting sub-system 620 is devoid of an electrical power source such that the detector heads 612 may be retracted after a power failure. In other embodiments, the retracting sub-system 620 uses a tool that is powered by a different electrical power source (e.g., battery) such that the detector heads 612 may be retracted after a power failure.

In the illustrated embodiment, the retracting sub-system 620 includes a retraction tool 622 and a link assembly 624 that extends between and operably couples the detector head 612 and the retraction tool 622. The retraction tool 622 is operably coupled to the detector head 612 such that the retraction tool 622 causes the detector head 612 to move away from the object when activated (e.g., engaged by the operator). The retraction tool 622 may be manually activated and powered by the operator (e.g., a crank or lever). The retraction tool 622 may also be manually activated but separately powered (e.g., a rotary tool, such as a power drill). In some embodiments, the retraction tool 622 is a manual handle in which the operator pulls or rotates the manual handle to move the detector head 612. For example, the manual handle may be a crank. In other embodiments, the retraction tool 622 is a rotary tool having a motor. Optionally, the motor may be battery-powered.

The link assembly 624 may include one or more elongated mechanical elements. For example, the link assembly 624 may include one or more cables 628 and/or one or more rigid segments, such as rigid beams (not shown). Each cable 628 includes an outer end 630 and an inner end 632. The link assembly 624 is connected to the movable arms 610. The link assembly 624 may move the movable arms 610 thereby retracting the detector heads 612. In some embodiments, the retraction tool 622 is accessible only after removing a panel 626. As shown, the panel 626 forms a part of an exterior to the stator 601. In other embodiments, the panel 626 may form part of an exterior of the gantry 602.

In some embodiments, the cables 628 may be similar to a rope, wire, cord, or line. In other embodiments, however, the cables 628 are flexible extension shafts that are configured to transmit rotary motion for retracting the detector assembly 608. The flexible extension shaft may be operably coupled to a motor (e.g., the detector motor). When the flexible extension shaft transmits rotary motion to the unpowered detector motor, the detector motor may rotate and thereby retract the detector assembly 608. The flexible extension shafts may include a rotating wire or coil which is flexible but has some torsional stiffness. A flexible extension shaft may or may not have a covering. The covering may be capable of bending but not capable of rotating.

For embodiments in which the cables 628 are flexible extension shafts that transmit rotary motion, the cables 628 may be operably coupled to the detector motor. When the cable 628 is operated to transmit rotary motion, the detector motor may be rotated by the cable 628 so as to retract the detector assembly 608. For example, the retraction tool 622 may be a power tool that is coupled to the outer end 630 of the cable 628. When activated, the power tool may rotate the outer end 630 of the cable 628 thereby rotating an opposite inner end 632 that is coupled to the detector motor.

For embodiments in which the cables 628 do not transmit rotary motion, the retraction tool 622 may be a crank that allows cables to be wound about, for example, a spool. As another example, the operator may pull on the retraction tool 622 in a release direction 625 thereby pulling the detector head 612. As can be seen in FIG. 13, each of the cables 628 is connected to a respective detector assembly 608. The outer ends 630 may be directly or indirectly connected to the retraction tool 622. The inner ends 632 may be directly or indirectly connected to the detector assembly 608. In the illustrated embodiment, the inner ends 632 are directly connected to movable arms 610. For embodiments in which the cables 628 are used to pull the detector assemblies 608 or, more specifically, the detector heads 612, the cables 628 may be pulled in a respective retract direction 636 as the retraction tool 622 is pulled in the release direction 625. The retract direction 636 is generally away from a center of the bore 604 and may be different for each detector assembly 608. As such, each of the cables 628 may be secured to the same retraction tool 622 that enables retracting all of the detector heads 612 simultaneously.

Although the retracting sub-system 620 is illustrated as including a retraction tool 622 and a link assembly 624, the retracting sub-system 620 may include additional or alternative mechanical components in other embodiments. For example, the retraction tool 622 may function as a release trigger that activates individual springs for retracting the respective detector heads 612. As another example, the retracting sub-system 620 may include a separate motor that is energized by a battery. The motor may rotate to wind up the cables 628, thereby pulling the movable arms 610 in the respective retract directions 636.

Figure 14:
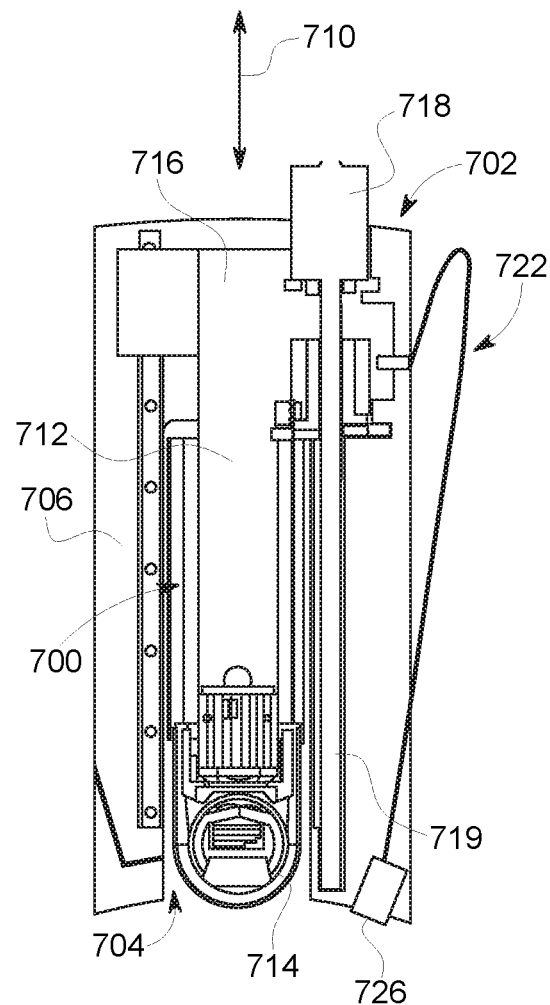
FIG. 14 is a schematic cross-sectional view of a detector assembly that includes a retracting sub-system in accordance with an embodiment.

FIG. 14 is a schematic cross-sectional view of a detector assembly 700 that includes a retracting sub-system 702 in accordance with an embodiment. In some embodiments, the detector assembly 700 may be one detector assembly of a plurality of other detector assemblies that are used by an NM imaging system, such as the various NM imaging systems described herein. The detector assembly 700 may be similar or identical to the detector assembly 300 (FIG. 5). As shown, the detector assembly 700 is positioned within a channel 704 of a gantry housing 706. The channel 704 is sized and shaped to allow the detector assembly 700 to move bi-directionally in a linear manner along an axis 710.

The detector assembly 700 includes a movable arm 712 and a detector head 714 operably coupled to the movable arm 712. The movable arm 712 includes a proximal end 716. As described with respect to the detector assembly 300, the movable arm 712 of the detector assembly 700 may move telescopically when driven by a detector motor 718 having a lead screw 719 such that the detector head 714 moves in a linear manner along the axis 710. Optionally, the detector head 714 may be operably coupled to another motor (not shown) for rotating or pivoting the detector head 714. Optionally, the detector head 714 may include a PSD (not shown) coupled to an end or face of the detector head 714.

The retracting sub-system 702 includes a release trigger 722 and a biasing element 724 (shown in FIG. 15) that is operably coupled to the release trigger 722. The release trigger 722 includes an operator-selectable element 726 that is configured to be pressed or pulled by an individual. Optionally, the user-selectable element 726 of the release trigger 722 is positioned within the bore or proximate to an entrance to the bore. When activated, the release trigger 722 causes the biasing element 724 to move from a first state (shown in FIG. 15) to a second state. The biasing element 724 drives the detector head 714 away from the object (not shown) within the bore when the biasing element 724 moves from the first state to the second state. Accordingly, one or more embodiments include a mechanical release trigger that is accessible to the operator. The release trigger may be activated (e.g., in an emergency) to activate a mechanical balancing device that moves the detector head away from the object.

Figure 15:
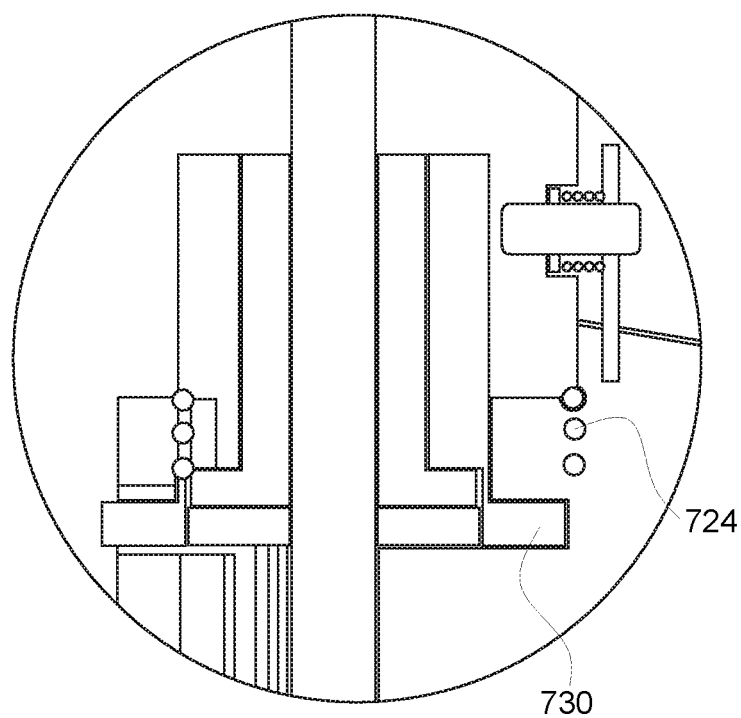
FIG. 15 is an enlarged portion of the cross-sectional view of the detector assembly shown in FIG. 14.

In the illustrated embodiment of FIG. 15, the biasing element 724 includes a spring. The spring is configured to be compressed when the biasing element 724 is in the first state such that a potential energy exists within the biasing element 724 for moving the biasing element 724 to the second state after the release trigger 722 is activated. In alternative embodiments, the biasing element 724 may pull the detector assembly 700 away from the object. For example, the biasing element 724 may be a spring that is stretched (or expanded) beyond a natural state. When the biasing element 724 is in the first state, a potential energy exists within the biasing element 724 for moving the biasing element 724 to the second state after the release trigger 722 is activated. When the biasing element 724 moves from the first state to the second state, the biasing element 724 urges the movable arm 712 away from a support surface 730. The support surface 730 may be, for example, part of the detector motor 718 or part of the gantry housing 706.

Figure 16:
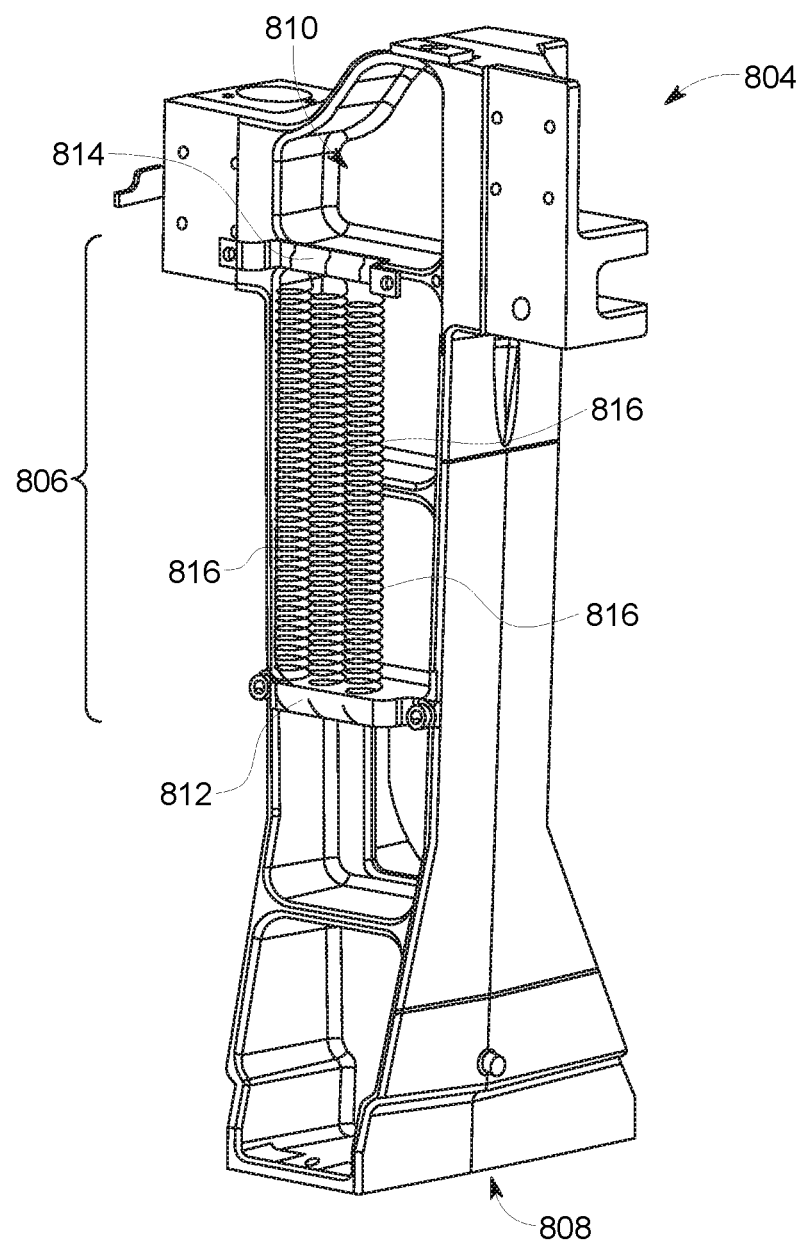
FIG. 16 is a rear perspective view of a movable arm having a retracting sub-system coupled thereto in accordance with an embodiment.

FIG. 16 is a rear perspective view of a movable arm 804 having a retracting sub-system 806 coupled thereto. The movable arm 804 may have similar features as the movable arms described herein and be used as part of a detector assembly 802 (shown in FIG. 17). The movable arm 804 includes a distal end 808 and a proximal end 810.

In the illustrated embodiment, the retracting sub-system 806 includes first and second coupling brackets 812, 814 and a plurality of elongated elements 816 extending between and joining the first and second coupling brackets 812, 814. The first coupling bracket 812 is secured to the movable arm 804. The second coupling bracket 814 is configured to be secured to a base support 820 that is secured to or part of a rotor 819 (shown in FIG. 17). In some embodiments, the elongated elements 816 are biasing elements. As shown, the elongated elements 816 are springs (e.g., tension springs or extension springs) that are designed to resist expansion. More specifically, as the elongated elements 816 are stretched or expanded beyond an unbiased state, a retraction force for returning the elongated elements to the unbiased state increases. Although the retracting sub-system 806 is illustrated as including a pair of coupling brackets, other embodiments may include only a single coupling bracket or may not utilize coupling brackets. For example, the elongated elements 816 may be configured to attach directly to the movable arm 804 and/or attach directly to the rotor 820.

Figure 17:
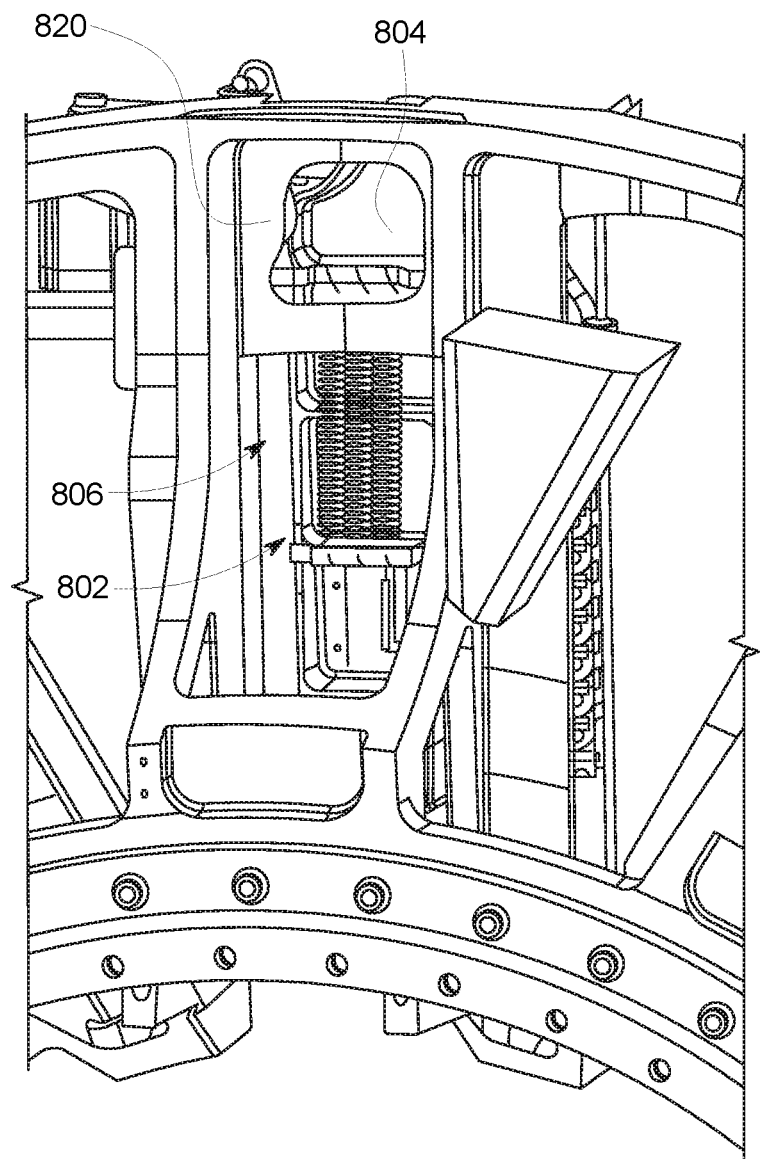
FIG. 17 is a rear perspective view of a detector assembly having the movable arm and retracting sub-system of FIG. 16 coupled to a gantry or rotor of an NM imaging system.
Figure 18:
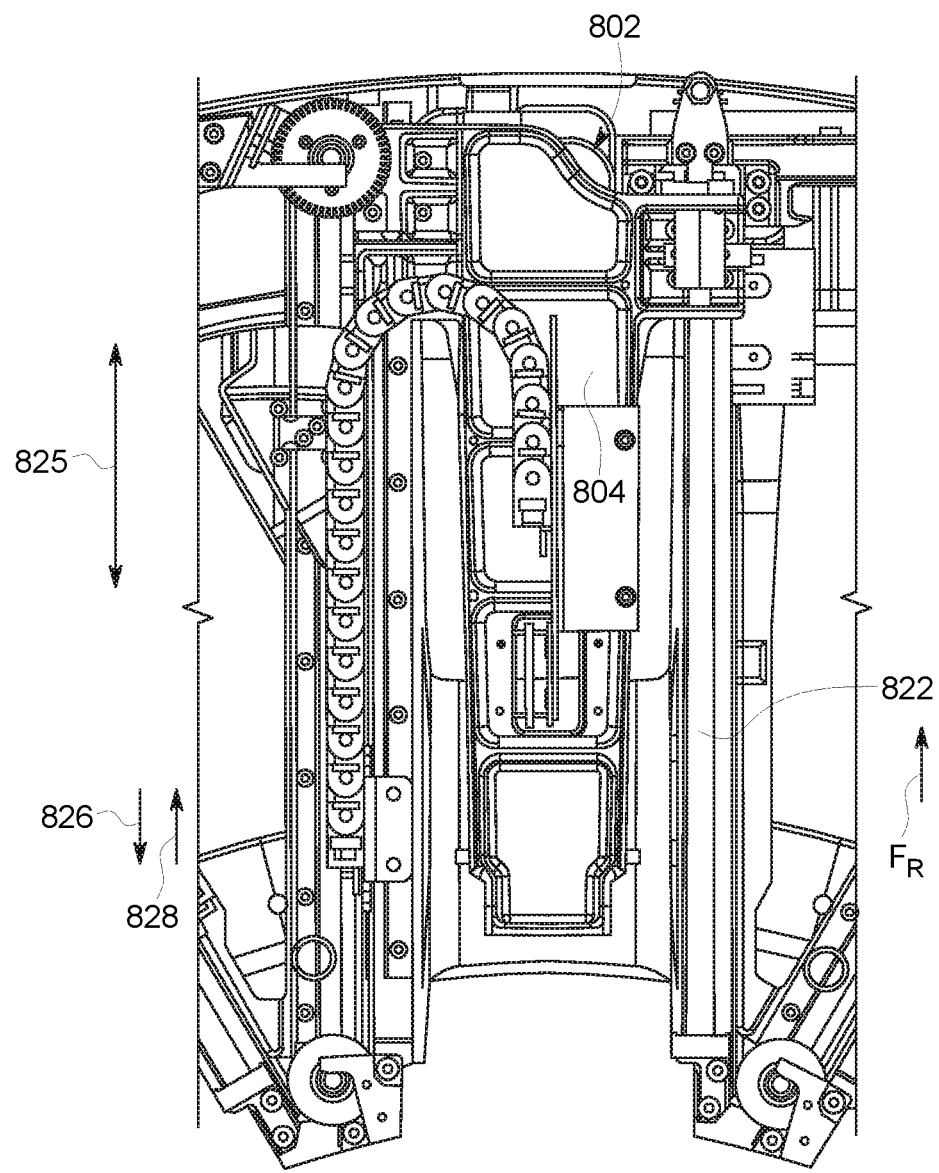
FIG. 18 is a front view of the detector assembly having the movable arm and retracting sub-system of FIG. 16 coupled to a gantry or rotor of an NM imaging system.

FIG. 17 is a rear perspective view of a detector assembly 802 having the movable arm 804 and the retracting sub-system 806. As shown in FIG. 17, the retracting sub-system 806 is coupled to the rotor 820 of an NM imaging system and the movable arm 804. FIG. 18 is a front view of the detector assembly 802 operably coupled to the rotor 820. A detector head is not shown in FIG. 18. Similar to the movable arm 712 (FIG. 14), the movable arm 804 is configured to move linearly along an axis 825 as guided by a lead screw 822. As the movable arm 804 moves in a first direction 826 toward the object, the elongated elements 816 (FIG. 16) stretch and a retraction force $F_R$ in an opposite second direction 828 increases.

As set forth herein, embodiments may utilize the elongated elements 816 when the detector motor is disabled. When the detector motor is disabled, the movable arm 804 may be permitted to move freely (e.g., back or forth) along the axis 825. As such, when the detector motor is disabled, the elongated elements 816 may be permitted to contract (or retract) thereby moving the movable arm 804 in the second direction 828 and away from the object.

In alternative embodiments, the elongated element 816 is not a spring. For example, the elongated element may be a cable, cord, or wire that is configured to be wound about a spool to retract the detector assembly.

Figure 19:
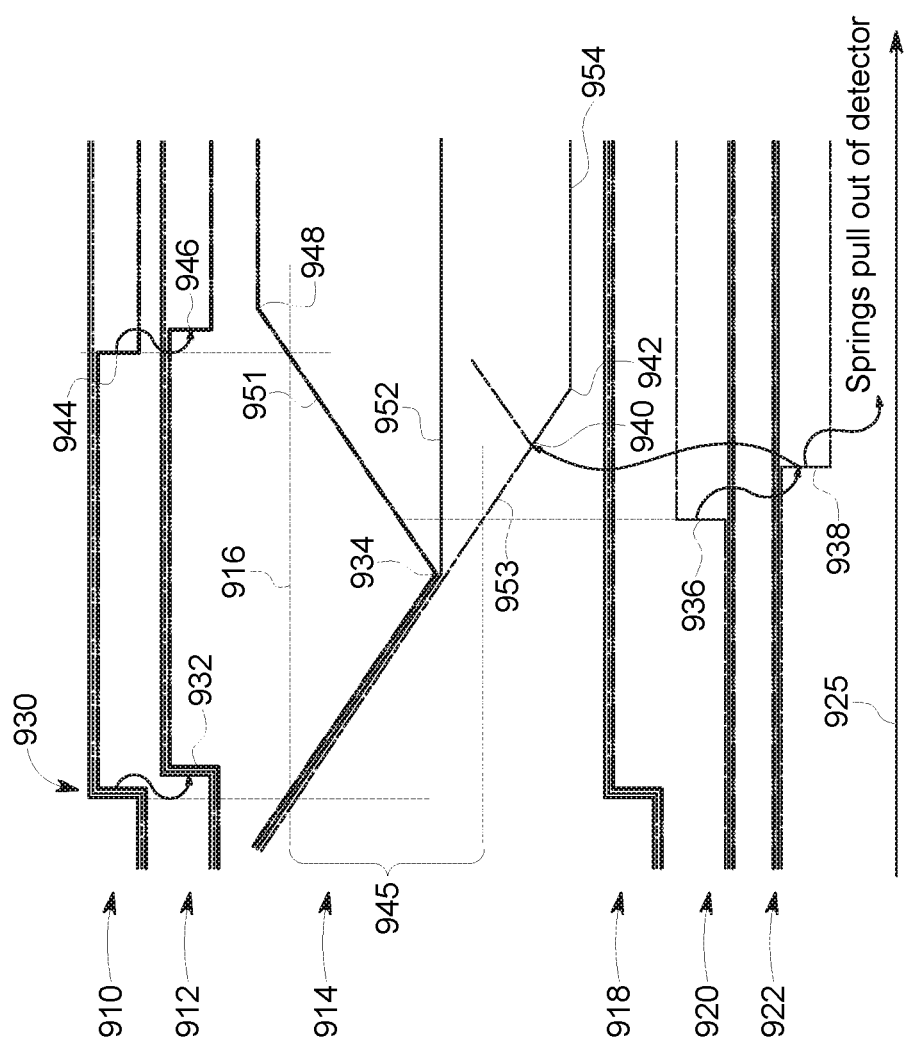
FIG. 19 is a graph illustrating different states of a positioning sub-system in accordance with an embodiment.

FIG. 19 is a graph illustrating an interaction between a positioning sub-system and a detector assembly. As described above, the positioning sub-system may include a detector motor that is operably coupled to a detector assembly, a motion controller configured to control the detector motor, and a PSD coupled to the detector assembly. In the embodiment of FIG. 19, a secondary circuit is configured to disable the detector motor (e.g., by cutting power to the detector motor and/or changing an operating state of the detector motor). The secondary circuit may generate a designated window and disable the detector motor in response to the designated window being exceeded.

FIG. 19 illustrates four different outcomes after a PSD is activated. Region 910 illustrates lines that identify a state of the PSD, which may be deactivated or activated. Region 912 illustrates a state of a release protocol, which may be deactivated or activated. Region 914 shows different lines representing a position of the detector head (or PSD) relative to the object. Line 916 identifies a position of the object. If the detector head is above the line 916, then the detector head has not engaged the object. If the detector head is below the line 916, then the detector head has engaged the object. Region 918 indicates a state of a designated window. Region 920 indicates whether the designated window has been exceeded. Region 922 indicates a bus voltage of a line the powers the detector motor. Axis 925 represents time, which increases as the axis 925 extends left-to-right.

At time point 930, a PSD coupled to the detector assembly is activated. For example, the PSD may engage the object or may determine that the object is within a predetermined distance of the PSD. The PSD transmits an output signal that initiates a release protocol at time point 932. A designated window 945 may be generated at time point 932. The designated window 945 may be generated by an integrated circuit (e.g., FPGA). The output signal may be transmitted to the motion controller or to the detector motor. As used herein, the phrase "transmitted to" includes direct communication and indirect communication. For example, the output signal may be transmitted to the system processor (or processing unit), which may then send an output signal to the motion controller or the detector motor. Alternatively, the output signal is communicated directly from the PSD to the detector motor or to the motion controller.

Line 951 represents a position of the detector head when the release protocol functions properly. More specifically, the detector motor will reverse directions and move the detector head away from the object 916. At time point 944, the detector head (or PSD) disengages from the object thereby deactivating the PSD and ending the release protocol at time point 946.

Line 952 represents a position of the detector head when the release protocol functions improperly, but the detector motor has been disabled. As shown in FIG. 19, the position of the detector head does not exceed the designated window 945. As such, the power is not cut and the retracting sub-system is not activated.

Line 953 represents a position of the detector head when the release protocol functions improperly and the designated window has been exceeded. At time point 936, it is determined (e.g., by the motion controller or integrated circuit or the system processor) that the designated window 945 has been exceeded. At time point 938, the bus voltage is cut. At time point 940, the detector motor is disabled. In some embodiment, after the bus voltage is cut the detector motor may permit the detector assembly to move freely (e.g., back and forth in radial direction) when a force is applied. For embodiments that include the retracting sub-system 806 of FIG. 16, the elongated elements (e.g., tension springs) pull the detector head in a direction away from the object (or in a direction toward the rotor). At time point 942, if the bus power was not cut, the torque limiter may be activated to prevent harm to the patient and damage to the detector assembly.

If the detector motor is not disabled, then the detector head continues to move such that the detector head presses against the object. At time point 942, the torque or load of the detector motor is exceeded thereby activating the torque limiter. When the torque limiter is activated, the detector head stops moving. Accordingly, embodiments may utilize a release protocol, a secondary circuit, a retracting sub-system (e.g., tension springs), and a torque limiter to control movement of the detector head.

Figure 20:
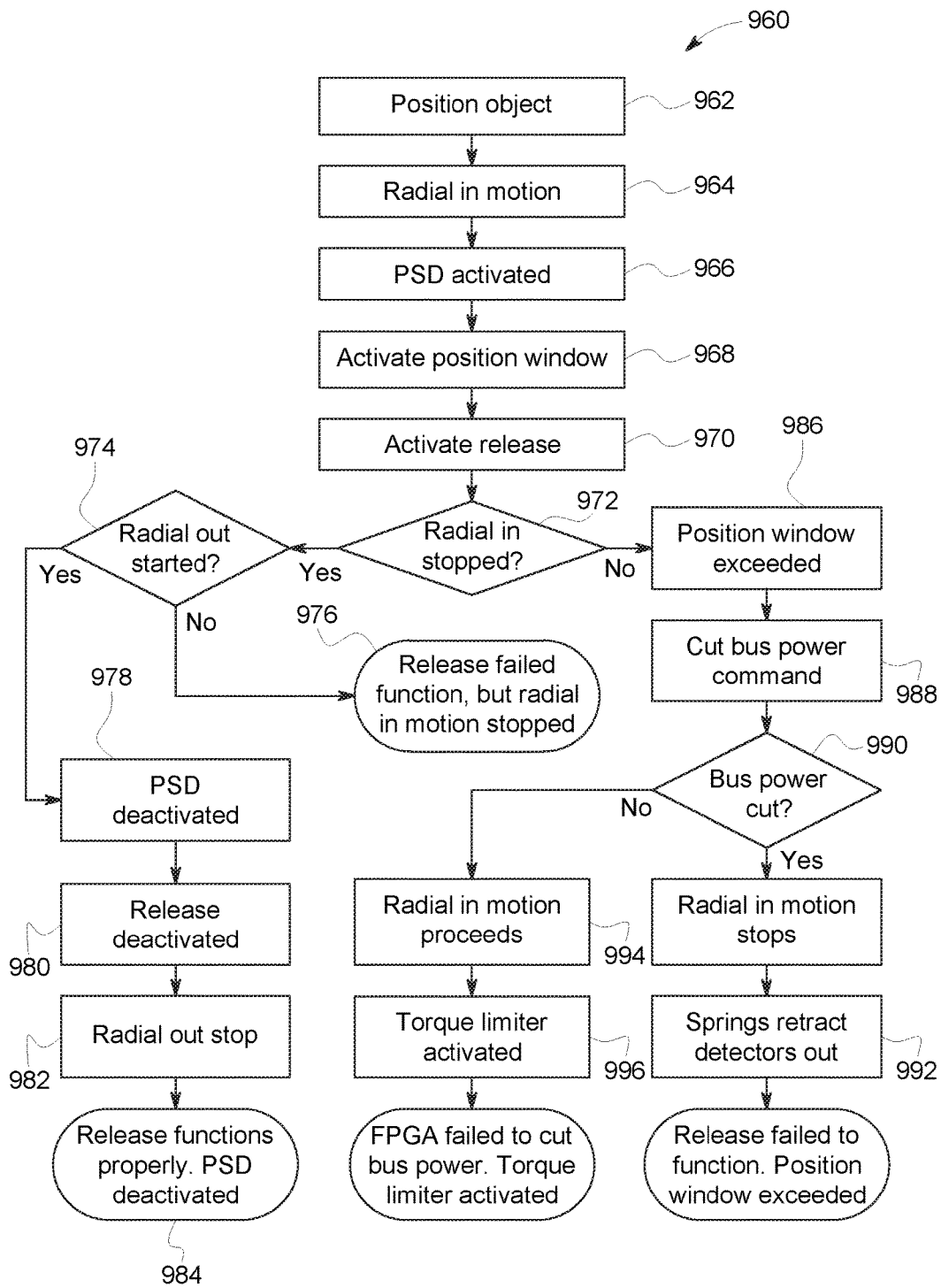
FIG. 20 is a flow chart illustrating a method in accordance with an embodiment.

FIG. 20 is a flow chart illustrating a method 960 in accordance with an embodiment. The method 960 may utilize an auto-release protocol, one or more of the retracting sub-systems described herein, and a torque limiter. The method 960 may be executed by the systems and devices set forth herein. The method 960 includes positioning, at 962, an object within a bore of a nuclear medicine (NM) imaging system. At 964, the detector motor controls the detector assembly to position the detector head relative to the object. For example, the detector motor may drive the detector assembly radially inward toward the object. At 966, it is determined that the detector head has engaged the object with the bore or is within a predetermined distance from the object. For example, the PSD may be activated.

At 968, a designated window is generated. In some embodiments, the designated window may be generated by the secondary circuit. At 970, a release protocol is initiated. At 972, it is determined whether the radially-inward motion of the detector assembly has stopped. If the radially-inward motion has stopped, then it is determined, at 974, whether the detector assembly has begun moving radially outward. If the detector assembly has not begun moving radially outward, then it is determined, at 976, that the release protocol has failed, but motion of the detector has stopped. An operator of the NM imaging system may be notified of this status.

If the detector assembly is moving radially outward, the PSD is deactivated at 978, the release protocol ends at 980, and the detector assembly stops moving at 982. Accordingly, the release protocol has functioned properly and the PSD has been deactivated. The operator of the NM imaging system may be notified of this status at 984.

Returning to 972, if it is determined that the radial motion of the detector assembly has not stopped, then the designated window is exceeded at 986 and the electrical power is cut at 988. At 990, it is determined whether the electrical power has been cut. If the electrical power has been cut, then the motion of the detector assembly has stopped. Optionally, a retracting sub-system may retract the detector assembly at 992. For example, tension springs may be permitted to pull the detector assembly away from the object.

If it is determined that the electrical power has not been cut at 990, then the motion of the detector assembly has not stopped and proceeds into the object at 994. At 996, a torque limiter may be activated. After the operation 996 or the operation 992, the operator may be notified of the status of the system.

Figure 21:
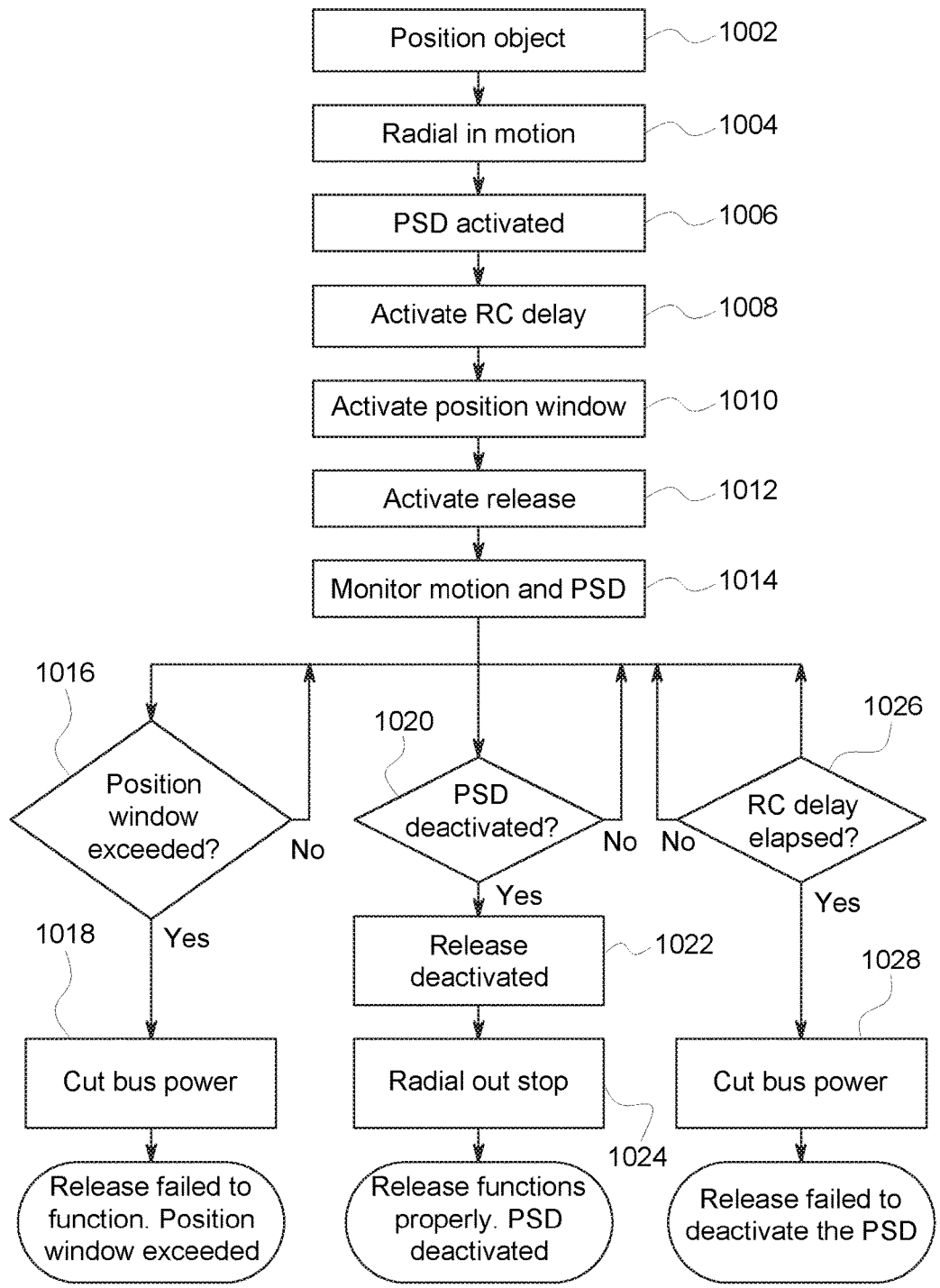
FIG. 21 is a flow chart illustrating a method in accordance with an embodiment.

FIG. 21 is a flow chart illustrating a method 1000 in accordance with an embodiment. The method 1000 may be executed by the systems and devices set forth herein. The method 1000 includes positioning, at 1002, an object within a bore of a nuclear medicine (NM) imaging system. At 1004, the detector motor controls the detector assembly to position the detector head relative to the object. For example, the detector motor may drive the detector assembly radially inward toward the object. At 1006, it is determined that the detector head has engaged the object with the bore or is within a predetermined distance from the object. For example, the PSD may be activated.

At 1008, a delay circuit (e.g., RC delay) is initiated. At 1010, a designated window is generated. In some embodiments, the designated window may be generated by the secondary circuit. A release protocol is initiated at 1012. At 1014, the detector assembly and PSD are monitored to determine whether the detector assembly has stopped moving or the PSD has been deactivated.

At 1016, it is determined whether the detector assembly has exceeded the designated window. If it is determined that the designated window has been exceeded, then the detector motor is disabled (e.g., electrical power is cut) at 1018. At 1020, it is determined whether the PSD has been deactivated. If it is determined that the PSD has been deactivated, then the release protocol will end at 1022 and the motion of the detector assembly will stop at 1024. At 1026, it is determined whether the delay circuit has elapsed. If the delay circuit has elapsed, the detector motor is disabled (e.g., bus voltage is cut) at 1028. Similar to the above, the system may notify the operator of the status of the system after the PSD was activated.

As used herein, a processor or a processing unit includes processing circuitry configured to perform one or more tasks, functions, or steps, such as those described herein. For instance, the processor may be a logic-based device that performs operations based on instructions stored on a tangible and non-transitory computer readable medium, such as memory. It may be noted that a "processor," as used herein, is not intended to necessarily be limited to a single processor or single logic-based device. For example, the processor may include a single processor (e.g., having one or more cores), multiple discrete processors, one or more application specific integrated circuits (ASICs), and/or one or more field programmable gate arrays (FPGAs). In some embodiments, the processor is an off-the-shelf device that is appropriately programmed or instructed to perform operations, such as the algorithms described herein.

The processor may also be a hard-wired device (e.g., electronic circuitry) that performs the operations based on hard-wired logic that is configured to perform the algorithms described herein. Accordingly, the processor may include one or more ASICs and/or FPGAs. Alternatively or in addition to the above, the processor may include or may be associated with a tangible and non-transitory memory having stored thereon instructions configured to direct the processor to perform the algorithms described herein.

It is noted that operations performed by the processor (e.g., operations corresponding to the methods/algorithms described herein, or aspects thereof) may be sufficiently complex that the operations may not be performed by a human being within a reasonable time period based on the intended application of the assay system. The processor may be configured to receive signals from the various subsystems and devices of the system or user inputs from the user. The processor may be configured to perform the methods described herein.

Processors may include or be communicatively coupled to memory. In some embodiments, the memory may include non-volatile memory. For example, the memory may be or include read-only memory (ROM), random-access memory (RAM), electrically erasable programmable read-only memory (EEPROM), flash memory, and the like. The memory may be configured to store data regarding operating parameters of the system.

In an exemplary embodiment, the processor executes a set of instructions that are stored in one or more storage elements, memories, and the like. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the system to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) imaging system comprising:
   a gantry including a bore that is sized and shaped to receive an object therein;
   a detector assembly coupled to the gantry, the detector assembly including a movable arm and a detector head that is coupled to the movable arm, the detector head configured to detect radiation emitted from the object within the bore; and
   a positioning sub-system including a motion controller and a detector motor that is operably coupled to the movable arm of the detector assembly, the motion controller configured to control the detector motor to move the movable arm and thereby position the detector head relative to the object, the positioning sub-system also including a proximity sensor device (PSD) coupled to the detector head, the PSD configured to be activated when the PSD engages the object or when the PSD is within a predetermined distance from the object, wherein, in response to being activated, the PSD is configured to transmit an output signal to the motion controller or to the detector motor that is configured to stop the detector motor from moving the detector head toward the object;
   wherein the NM imaging system also includes a secondary circuit that, in response to the PSD being activated, is configured to determine whether the detector head has stopped moving toward the object and, in response to determining that the detector head has not stopped moving toward the object, is configured to disable the detector motor.

2. The NM imaging system of claim 1, wherein the secondary circuit is configured to disable the detector motor by at least one of (a) disconnecting the detector motor from an electrical power source or (b) changing the detector motor from an active state to an inactive state.

3. The NM imaging system of claim 2, wherein the secondary circuit includes non-programmable circuitry or non-reprogrammable circuitry that disconnects the detector motor from an electrical power source after a designated time period from activation of the PSD.

4. The NM imaging system of claim 2, wherein the detector head is configured to move relative to a base support, the NM imaging system further comprising a retracting sub-system that includes an elongated element joining the base support and the detector assembly, the retracting sub-system configured to apply a retraction force to the movable arm in a direction toward the base support as the detector head moves from the base support toward the object, the retraction force configured to pull the movable arm toward the base support after the detector motor is disabled by the secondary circuit, the detector motor configured to permit the movable arm to be pulled toward the base support after the detector motor is disabled by the secondary circuit.

5. The NM imaging system of claim 1, wherein the motion controller of the positioning sub-system includes a processor and a storage medium that is configured to store programmed instructions accessible by the processor, wherein, responsive to execution of the programmed instructions and receiving the output signal, the processor is configured to transmit a command signal to the detector motor to stop the detector motor from moving the detector head toward the object, wherein the secondary circuit is separate and distinct from the motion controller and includes non-programmable circuitry or non-reprogrammable circuitry.

6. The NM imaging system of claim 1, wherein the secondary circuit is configured to determine whether the detector head has stopped moving toward the object within a designated window, the designated window being a function of at least one of distance or time and beginning upon activation of the PSD, wherein, upon determining that the detector head has not stopped moving toward the object within the designated window, the secondary circuit is configured to disable the detector motor.

7. The NM imaging system of claim 6, wherein the secondary circuit includes a delay circuit that is configured to disconnect the detector motor from an electrical power source upon determining that the detector head has not stopped moving toward the object within the designated window, the delay circuit configured to be deactivated if the detector head stops moving toward the object within the designated window.

8. The NM imaging system of claim 1, further comprising a retracting sub-system that is distinct from the positioning sub-system, the retracting sub-system being operably coupled to the detector assembly, the retracting sub-system enabling movement of the detector head away from the object.

9. The NM imaging system of claim 8, wherein the retracting sub-system is devoid of an electrical power source for moving the detector head, the retracting sub-system including a release trigger and a biasing element that is operably coupled to the release trigger, the release trigger, when activated, being configured to cause the biasing element to move from a first state to a second state, the biasing element configured to drive the detector head away from the object when the biasing element moves from the first state to the second state.

10. The NM imaging system of claim 8, wherein the retracting sub-system is devoid of an electrical power source for moving the detector head, the retracting sub-system including a manual handle and a link assembly that extends between and operably couples the detector head and the manual handle, the manual handle configured to be moved by an operator, the manual handle being operably coupled to the detector head such that the manual handle causes the detector head to move away from the object within the bore when activated by the operator.

11. The NM imaging system of claim 1, wherein the secondary circuit includes non-programmable circuitry or non-reprogrammable circuitry, the secondary circuit being configured to determine whether the detector head has stopped moving toward the object within a designated window after activation of the PSD, the designated window being a function of at least one of distance or time.

12. The NM imaging system of claim 1, wherein the secondary circuit includes an integrated circuit and a delay circuit, the integrated circuit configured to disable the detector motor in response to determining that the detector head has not stopped moving toward the object within a designated window, the designated window being a function of at least one of distance or time, the delay circuit cutting power to the detector motor if the integrated circuit fails to disable the detector motor.

13. The NM imaging system of claim 1, wherein the secondary circuit disconnects the detector motor from an electrical power source after a designated time period from activation of the PSD, the NM imaging system further comprising biasing elements operably coupled to the detector head, the biasing elements generating a retraction force as the detector head is moved toward the object, the springs pulling the detector head away from the object after the detector motor is disconnected from the electrical power source.

14. The NM imaging system of claim 13, further comprising a torque limiter coupled to the detector motor, the torque limiter decoupling a driven component of the detector motor with respect to a load in response to the load exceeding a designated value.

15. A nuclear medicine (NM) imaging system comprising:
a gantry including a bore that is sized and shaped to receive an object therein;
a detector assembly coupled to the gantry, the detector assembly including a movable arm and a detector head that is coupled to the movable arm, the detector head configured to detect radiation emitted from the object within the bore; and
a positioning sub-system including a motion controller and a detector motor that is operably coupled to the movable arm of the detector assembly, the motion controller configured to control the detector motor to position the detector head relative to the object;
wherein the NM imaging system further comprises a retracting sub-system that is operably coupled to the detector assembly, the retracting sub-system being distinct from the positioning sub-system and configured to enable movement of the detector head away from the object within the bore;
wherein the retracting sub-system includes a release trigger and a biasing element that is operably coupled to the release trigger, the release trigger, when activated, configured to cause the biasing element to move from a first state to a second state, the biasing element configured to drive the detector head away from the object within the bore when the biasing element moves from the first state to the second state.

16. The NM imaging system of claim 15, wherein the biasing element includes a spring, the spring being compressed or stretched when the biasing element is in the first state such that a potential energy exists within the biasing element for moving the biasing element to the second state after the release trigger is activated.

17. The NM imaging system of claim 15, wherein the release trigger is positioned within the bore or proximate to an entrance to the bore.

18. A nuclear medicine (NM) imaging system comprising:
a gantry including a bore that is sized and shaped to receive an object therein;
a detector assembly coupled to the gantry, the detector assembly including a movable arm and a detector head that is coupled to the movable arm, the detector head configured to detect radiation emitted from the object within the bore; and
a positioning sub-system including a motion controller and a detector motor that is operably coupled to the movable arm of the detector assembly, the motion controller configured to control the detector motor to position the detector head relative to the object;
wherein the NM imaging system further comprises a retracting sub-system that is operably coupled to the detector assembly, the retracting sub-system being distinct from the positioning sub-system and configured to enable movement of the detector head away from the object within the bore;
wherein the retracting sub-system includes a manual handle and a link assembly that extends between and operably couples the detector head and the manual handle, the manual handle being operably coupled to the detector head such that the manual handle causes the detector head to move away from the object within the bore when activated.

19. The NM imaging system of claim 18, wherein the retracting sub-system is devoid of an electrical power source for moving the detector head.

20. The NM imaging system of claim 18, wherein the positioning sub-system includes proximity sensor detector (PSD) coupled to detector head, the PSD configured to be activated when the PSD engages the object or when the PSD is within a predetermined distance from the object, the positioning sub-system configured to automatically stop movement of the detector head when the PSD of the respective detector head is activated;
the NM imaging system further comprising a secondary circuit communicatively coupled to the PSDs, wherein, responsive to one or more of the PSDs being activated, the secondary circuit is configured to determine whether the detector head of the activated PSD has stopped moving toward the object and, if the secondary circuit determines that the detector head of the activated PSD has not stopped moving toward the object, the secondary circuit is configured to disable the detector motor that moves the detector head of the activated PSD.

* * * * *